United States Patent
Tojo et al.

(10) Patent No.: US 7,556,926 B2
(45) Date of Patent: Jul. 7, 2009

(54) METHODS FOR SCREENING INSULIN-SENSITIZING AGENTS

(75) Inventors: Hideaki Tojo, Ibaraki (JP); Tsutomu Henta, Osaka (JP); Reiko Sasada, Kyoto (JP)

(73) Assignee: Takeda Pharmaceuticals Company Ltd., Osaka (JP)

( * ) Notice: Subject to any disclaimer, the term of this patent is extended or adjusted under 35 U.S.C. 154(b) by 120 days.

(21) Appl. No.: 10/515,720

(22) PCT Filed: May 22, 2003

(86) PCT No.: PCT/JP03/06399

§ 371 (c)(1), (2), (4) Date: Nov. 23, 2004

(87) PCT Pub. No.: WO03/099331

PCT Pub. Date: Dec. 4, 2003

(65) Prior Publication Data

US 2006/0014679 A1  Jan. 19, 2006

(30) Foreign Application Priority Data

May 24, 2002 (JP) .............................. 2002-151360

(51) Int. Cl.
*G01N 33/55* (2006.01)
*G01N 33/554* (2006.01)
*A61K 38/24* (2006.01)

(52) U.S. Cl. .................. 435/7.1; 436/519; 530/399

(58) Field of Classification Search ........................ None
See application file for complete search history.

(56) References Cited

U.S. PATENT DOCUMENTS 5,468,614 A * 11/1995 Fields et al. .................. 435/6

6,878,687 B1 * 4/2005 Ruben et al. .................. 514/12
2003/0165875 A1 * 9/2003 Colonna et al. ................ 435/6

FOREIGN PATENT DOCUMENTS

| JP | 2001-340080 | 12/2001 |
|----|----|----|
| WO | WO 98/39446 | 9/1998 |
| WO | WO 00/58463 | 10/2000 |
| WO | WO 01/32637 A1 | 5/2001 |
| WO | WO 01/87341 A1 | 11/2001 |

OTHER PUBLICATIONS

Mickle, JE. Genotype-phenotype relationships in cystic fibrosis. Med. Clin. N. America. 2000. vol. 84, No. 3, p. 597-607.*
Barness L.A., et al. Obesity: Genetic, molecular, and environmental aspects. Am. J. Med Genetics, Part A. 2007, vol. 143A, p. 3016-3034.*
Brod, S.A., et al. Ingested interferon-a suppresses Type I diabetes in non-obese diabetic mice. Diabetologia. 1998, vol. 41, p. 1227-1232.*
Bouchon et al., "Cutting Edge: inflammatory Responses Can Be Triggered by TREM-1, a Novel Receptor Expressed on Neutrophils and Monocytes", The Journal of Immunology, pp. 4991-4995 (2000).
Daws et al., "Cloning and characterization of a novel mouse myeloid DAP12-associated receptor family", Eur. J. Immunol., 31:783-791 (2001).
Bouchon et al., "A DAP12-mediated pathway Regulates Expresion of CC Chemokine Receptor 7 and Maturation of the Human Dendritic Cells", J. Exp. Med., 194(8):1111-1122 (2001).

* cited by examiner

*Primary Examiner*—Robert Landsman
*Assistant Examiner*—Bruce D Hissong
(74) *Attorney, Agent, or Firm*—Edwards Angell Palmer & Dodge LLP; David G. Conlin, Esq.; Kathryn A. Piffat, Esq.

(57) ABSTRACT

A compound or its salt inhibiting the activity of a protein having an amino acid sequence which is the same or substantially the same amino acid sequence as the amino acid sequence represented by SEQ ID NO: 1, an extracellular domain of the protein above, an antibody, an antisense polynucleotide, etc. are usable as insulin-sensitizing agents and preventives and/or remedies for diabetes, obesity, hyperlipemia, arteriosclerosis, hypertension, heart disease, and so on.

17 Claims, No Drawings

METHODS FOR SCREENING INSULIN-SENSITIZING AGENTS

CROSS-REFERENCES TO RELATED APPLICATIONS

The present application is the 35 U.S.C. §371 national stage of PCT application PCT/JP03/06399, filed May 22, 2003, which claims benefit of Japanese application 2002-151360, filed May 24, 2002, the disclosures of all of which are incorporated herein by reference.

TECHNICAL FIELD

The present invention relates to agents for sensitizing insulin, diagnostic agents therefor, agents for the prevention and/or treatment of diabetes and diagnostic agents therefor, as well as screening thereof, and so on.

BACKGROUND ART

Insulin resistance is a pathological condition that insulin resistance decreases in tissues and especially in type II diabetes, is a major cause associated with the development or progress of diabetes, in addition to impaired insulin secretion. In general, many patients with diabetes accompanying obesity have insulin resistance. Thus, insulin resistance is considered to be deeply involved in obesity. It is further known that insulin resistance is observed not only in diabetes but also in disorders caused by abnormalities in lipid metabolism such as arteriosclerosis, etc. (Saltiel, A. R., Cell, 104, 517-529, 2001).

While the mechanism of insulin resistance largely remains unknown yet, a suggestion, as one point of view, is made on a similarity to the mechanism of inflammation in animal test or on an experimental level using a culture cell system. For example, it is reported that when lipopolysaccharide (LPS) was administered to pregnant rats, the offspring were found to develop obesity and insulin resistance at adult age (Nilsson et al., Endocrinol., 142, 2622-2630, 2001); TNF-α, which is one of inflammatory cytokines, is produced and/or secreted more in obese adipocytes to inhibit the action of insulin (Hotamisligil G. S. et al., Science, 259, 87-91, 1993); moreover, thiazolidine derivatives, which are insulin-sensitizing agents, have an anti-inflammatory action (Pasceri, V. et al., Circulation, 101, 235-238, 2000) and so on. Furthermore, fluctuation in expression of several proteins associated with inflammatory reactions, including LPS-binding protein are noted also in ob/ob mice as obesity model mice (Soukas, A. et al., Genes Develop, 14, 963-980, 2000).

Triggering receptor expressed on myeloid cells 2 (TREM-2) is a membrane protein of one transmembrane type belonging to the immunoglobulin superfamily found to be a homolog protein of TREM-1 thought to be involved in inflammatory reactions (Bauchon, A. et al., J. Immunol., 164, 4991-4995, 2000, Daws M. R. et al., Eur. J. Immunol., 31, 783-791, 2001). TREM-1 is abundantly expressed on neutrophils and on monocytes. It is known that its expression results in amplifying inflammation by promoting the secretion of lipopolysaccharide-induced TNF-α or interleukin-1β and by inhibiting the expression, acute inflammatory response can be suppressed in mice (Bauchon, A. et al., Nature, 410, 1103-1107, 2001). It is reported that TREM-2 interacts with DAP12 as in TREM-1 to effect signal transduction (Daws M. R. et al., Eur. J. Immunol., 31, 783-791, 2001); TREM-2 induces the expression of CC chemokine receptor 7 (CCR7) in dendritic cells or macrophages to take part in maturing of dendritic cells (Bouchon, A. et al., J. Exp. Med., 194, 1111-1122, 2001); and TREM-2 is associated with NO production (Daws M. R. et al., Eur. J. Immunol., 31, 783-791, 2001).

Safe and excellent pharmaceuticals for sensitizing insulin have been earnestly awaited.

DISCLOSURE OF THE INVENTION

The present inventors made extensive investigations to solve the foregoing problems and as a result, found TREM-2 from the group of genes, which expression was enhanced in adipocytes of KKA$^y$ mice as a model animal with obesity and insulin resistance (Nishimura, M., Exp. Animal, 18, 147-157, 1969). Based on this finding, the inventors made further studies and have thus come to accomplish the present invention.

That is, the present invention provides the following features.

(1) An insulin-sensitizing agent which comprises a compound or its salt that inhibits the activity of a protein containing the same or substantially the same amino acid sequence as the amino acid sequence represented by SEQ ID NO: 1, its partial peptide, or a salt thereof.

(2) An insulin-sensitizing agent which comprises a compound or its salt that inhibits the expression of a gene for a protein containing the same or substantially the same amino acid sequence as the amino acid sequence represented by SEQ ID NO: 1.

(3) An insulin-sensitizing agent which comprises a compound or its salt that inhibits the expression of a protein containing the same or substantially the same amino acid sequence as the amino acid sequence represented by SEQ ID NO: 1.

(4) The insulin-sensitizing agent according to (1) through (3), which is an agent for the prevention and/or treatment of diabetes, obesity, hyperlipemia, arteriosclerosis, hypertension or heart disease.

(4a) The insulin-sensitizing agent according to (1) through (3), which is an agent for the prevention and/or treatment of diabetes.

(4b) The insulin-sensitizing agent according to (1) through (3), which is an agent for the prevention and/or treatment of hyperlipemia.

(4c) The insulin-sensitizing agent according to (1) through (3), which is an agent for the prevention and/or treatment of arteriosclerosis.

(5) An insulin-sensitizing agent which comprises an extracellular domain of a protein containing the same or substantially the same amino acid sequence as the amino acid sequence represented by SEQ ID NO: 1; or a salt thereof.

(6) The insulin-sensitizing agent according to (5), wherein the extracellular domain is a partial peptide containing the 14-167 amino acid sequence in the amino acid sequence represented by SEQ ID NO: 1.

(7) An agent for the prevention and/or treatment of diabetes, obesity, hyperlipemia, arteriosclerosis, hypertension or heart disease which comprises an extracellular domain of a protein containing the same or substantially the same amino acid sequence as the amino acid sequence represented by SEQ ID NO: 1; or a salt thereof.

(8) An antisense polynucleotide containing the entire or part of a base sequence complementary or substantially complementary to a base sequence of a polynucleotide encoding a protein containing the same or substantially the same amino acid sequence represented by SEQ ID NO: 1 or its partial peptide.

(9) An insulin-sensitizing agent which comprises the antisense polynucleotide according to (8).

(10) An agent for the prevention and/or treatment of diabetes, obesity, hyperlipemia, arteriosclerosis, hypertension or heart disease, which comprises the antisense polynucleotide according to (8).

(11) An insulin-sensitizing agent which comprises an antibody to a protein containing the same or substantially the same amino acid sequence as the amino acid sequence represented by SEQ ID NO: 1, its partial peptide, or a salt thereof.

(12) An agent for the prevention and/or treatment of diabetes, obesity, hyperlipemia, arteriosclerosis, hypertension or heart disease, which comprises an antibody to a protein containing the same or substantially the same amino acid sequence as the amino acid sequence represented by SEQ ID NO: 1, its partial peptide, or a salt thereof.

(13) A diagnostic agent for insulin resistance, which comprises an antibody to a protein containing the same or substantially the same amino acid sequence as the amino acid sequence represented by SEQ ID NO: 1, its partial peptide, or a salt thereof.

(14) A diagnostic agent for diabetes, obesity, hyperlipemia, arteriosclerosis, hypertension or heart disease, which comprises an antibody to a protein containing the same or substantially the same amino acid sequence as the amino acid sequence represented by SEQ ID NO: 1, its partial peptide, or a salt thereof.

(15) A diagnostic agent for insulin resistance, which comprises a polynucleotide encoding a protein containing the same or substantially the same amino acid sequence represented by SEQ ID NO: 1, or its partial peptide.

(16) A diagnostic agent for diabetes, obesity, hyperlipemia, arteriosclerosis, hypertension or heart disease, which comprises a polynucleotide encoding a protein containing the same or substantially the same amino acid sequence represented by SEQ ID NO: 1, or its partial peptide.

(17) A method of screening an insulin-sensitizing agent, which comprises using a protein containing the same or substantially the same amino acid sequence as the amino acid sequence represented by SEQ ID NO: 1, its partial peptide, or a salt thereof.

(18) A method of screening an antagonist of a protein containing the same or substantially the same amino acid sequence as the amino acid sequence represented by SEQ ID NO: 1, or a salt of the protein, which comprises using (i) the protein, its partial peptide, or a salt thereof and (ii) a ligand to the protein, its partial peptide, or a salt thereof.

(19) A method of screening an insulin-sensitizing agent, which comprises using (i) a protein containing the same or substantially the same amino acid sequence as the amino acid sequence represented by SEQ ID NO: 1, its partial peptide, or a salt thereof and (ii) a ligand to the protein, its partial peptide, or a salt thereof.

(20) A kit for screening an insulin-sensitizing agent, which comprises a protein containing the same or substantially the same amino acid sequence as the amino acid sequence represented by SEQ ID NO: 1, its partial peptide, or a salt thereof.

(21) A method of screening an insulin-sensitizing agent, which comprises using a polynucleotide encoding a protein containing the same or substantially the same amino acid sequence as the amino acid sequence represented by SEQ ID NO: 1, or its partial peptide.

(22) A kit for screening an insulin-sensitizing agent which comprises a polynucleotide encoding a protein containing the same or substantially the same amino acid sequence as the amino acid sequence represented by SEQ ID NO: 1, or its partial peptide.

(23) An insulin-sensitizing agent, which is obtainable using the screening method according to (17), (19) or (21), or the screening kit according to (20) or (22).

(24) The screening method according to (17), (18), (19) or (21), wherein substantially the same amino acid sequence as the amino acid sequence represented by SEQ ID NO: 1 is the amino acid sequence represented by SEQ ID NO: 2.

(24a) The screening kit according to (20) or (22), wherein substantially the same amino acid sequence as the amino acid sequence represented by SEQ ID NO: 1 is the amino acid sequence represented by SEQ ID NO: 2.

(25) A method of screening an agent for the prevention and/or treatment of diabetes, obesity, hyperlipemia, arteriosclerosis, hypertension or heart disease, which comprises using a protein containing same or substantially the same amino acid sequence as the amino acid sequence represented by SEQ ID NO: 1, its partial peptide, or a salt thereof.

(25a) A method of screening an agent for the prevention and/or treatment of diabetes, obesity, hyperlipemia, arteriosclerosis, hypertension or heart disease, which comprises using (i) a protein containing same or substantially the same amino acid sequence as the amino acid sequence represented by SEQ ID NO: 1, its partial peptide, or a salt thereof, and (ii) a ligand to the protein, its partial peptide, or a salt thereof.

(26) A kit for screening an agent for the prevention and/or treatment of diabetes, obesity, hyperlipemia, arteriosclerosis, hypertension or heart disease, which comprises a protein containing same or substantially the same amino acid sequence as the amino acid sequence represented by SEQ ID NO: 1, its partial peptide, or a salt thereof.

(27) A method of screening an agent for the prevention and/or treatment of diabetes, obesity, hyperlipemia, arteriosclerosis, hypertension or heart disease, which comprises using a polynucleotide encoding a protein containing same or substantially the same amino acid sequence as the amino acid sequence represented by SEQ ID NO: 1, or its partial peptide.

(28) A kit for screening an agent for the prevention and/or treatment of diabetes, obesity, hyperlipemia, arteriosclerosis, hypertension or heart disease, which comprises a polynucleotide encoding a protein containing same or substantially the same amino acid sequence as the amino acid sequence represented by SEQ ID NO: 1, or its partial peptide.

(29) An agent for the prevention and/or treatment of diabetes, obesity, hyperlipemia, arteriosclerosis, hypertension or heart disease, which is obtainable using the screening method according to (25) or (27), or the screening kit according to (26) or (28).

(29a) An agent for the prevention and/or treatment of diabetes, which is obtainable using the screening method according to (25) or (27), or the screening kit according to (26) or (28).

(29b) The screening method according to (25) or (27), wherein substantially the same amino acid sequence represented by SEQ ID NO: 1 is the amino acid sequence represented by SEQ ID NO: 2.

(29c) The screening kit according to (26) or (28), wherein substantially the same amino acid sequence represented by SEQ ID NO: 1 is the amino acid sequence represented by SEQ ID NO: 2.

(30) A method of sensitizing insulin, which comprises administering to a mammal an effective dose of a compound or its salt that inhibits the activity of a protein containing same or substantially the same amino acid sequence as the amino acid sequence represented by SEQ ID NO: 1, its partial peptide, or a salt of the protein, or a compound or its salt that inhibits the expression of a gene for the protein.

(31) A method of preventing and/or treating diabetes, which comprises administering to a mammal an effective dose of a compound or its salt that inhibits the activity of a protein containing same or substantially the same amino acid sequence as the amino acid sequence represented by SEQ ID NO: 1, its partial peptide, or a salt of the protein, or a compound or its salt that inhibits the expression of a gene for the protein.

(32) Use of a compound or its salt that inhibits the activity of a protein containing same or substantially the same amino acid sequence as the amino acid sequence represented by SEQ ID NO: 1, its partial peptide, or a salt of the protein, or a compound or its salt that inhibits the expression of a gene for the protein, to manufacture an insulin-sensitizing agent.

(33) Use of a compound or its salt that inhibits the activity of a protein containing same or substantially the same amino acid sequence as the amino acid sequence represented by SEQ ID NO: 1, its partial peptide, or a salt of the protein, or a compound or its salt that inhibits the expression of a gene for the protein, to manufacture an agent for the prevention and/or treatment of diabetes.

BEST MODE FOR CARRYING OUT THE INVENTION

The protein containing same or substantially the same amino acid sequence as the amino acid sequence represented by SEQ ID NO: 1 (hereinafter sometimes referred to as the protein or the present invention or the protein used in the present invention) may be any protein derived from any cell of human and warm-blooded animals (e.g., guinea pigs, rats, mice, rabbits, swine, sheep, bovine, monkey, etc.); any cell (e.g., hepatocytes, splenocytes, nerve cells, glial cells, β cells of pancreas, bone marrow cells, mesangial cells, Langerhans' cells, epidermic cells, epithelial cells, goblet cells, endothelial cells, smooth muscle cells, fibroblasts, fibrocytes, myocytes, adipocytes, immune cells (e.g., macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.); or any tissues where such cells are present, such as brain or any of brain regions (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gallbladder, bone marrow, adrenal gland, skin, muscle, lung, gastrointestinal tract (e.g., large intestine and small intestine), blood vessel, heart, thymus, spleen, submandibular gland, peripheral blood, prostate, testicle, testis, ovary, placenta, uterus, bone, joint, skeletal muscle, etc.; the proteins may also be synthetic proteins.

The amino acid sequence which has substantially the same amino acid sequence as that represented by SEQ ID NO: 1 includes an amino acid sequence having at least about 60% homology, preferably at least about 70% homology, more preferably at least about 80% homology, much more preferably at least about 90% homology and most preferably at least about 95% homology, to the amino acid sequence represented by SEQ ID NO: 1.

As the protein which contains substantially the same amino acid sequence as that represented by SEQ ID NO: 1, for example, a protein having substantially the same amino acid sequence as that represented by SEQ ID NO: 1 and preferably having the activity substantially equivalent to the amino acid sequence represented by SEQ ID NO: 1, etc. are preferred.

Examples of the protein which contains substantially the same amino acid sequence as that represented by SEQ ID NO: 1 include a protein containing the amino acid sequence represented by SEQ ID NO: 2, and the like.

Examples of the substantially equivalent activity described above include a signal transduction activity [e.g., the intracellular signal transduction activity of the protein of the present invention (preferably TREM-2), etc.], a ligand binding activity [e.g., the ligand binding activity of the protein of the present invention (preferably TREM-2) to a ligand or a low molecular substance; etc.] and the like. The term substantially equivalent is used to mean that the activities are the same in nature (e.g., physiologically or pharmacologically). Therefore, although it is preferred that activities such as the signal transduction and ligand binding activities, etc. be equivalent (e.g., about 0.01- to about 100-fold, preferably about 0.1- to about 10-fold, more preferably about 0.5- to about 2-fold), quantitative factors such as a level of these activities, a molecular weight of the protein, etc. may be different.

The signal transduction and ligand binding activities can be determined according to publicly known methods, e.g., the method described in J. Exp. Med., 194, 1111-1122, 2001, or methods with some modifications thereof.

Signal of the protein of the present invention (preferably TREM-2) causes phosphorylation on, e.g., TREM-2, activates ERK (extracellular signal-related protein) and promotes secretion of inflammatory cytokine (e.g., TNF-α, etc.). Thus, the signal transduction activity described above is determined by adding to, e.g., cells expressed with the protein of the present invention (e.g., TREM-2-expressed animal cells), (a) a ligand-containing fluid such as a microorganism lysate, a microorganism supernatant, an eukaryotic cell lysate, an eukaryotic cell supernatant, etc., (b) a ligand itself, (c) a substance having a binding activity to the protein of the present invention equivalent to a naturally occurring ligand, or (d) an antibody activating the protein of the present invention (e.g., TREM-2), if necessary, and assaying (1) the level of phosphorylated ERK produced, (2) the level of TNF-α produced and secreted extracellularly or (3) the level of phosphorylated TREM-2 produced.

The level of phosphorylated ERK or TNF-α produced can be assayed by publicly known methods (e.g., western blotting, EIA, etc.) using an anti-phosphorylated ERK antibody or an anti-TNF-α antibody. The level of phosphorylated TREM-2 produced can be assayed by publicly known methods (e.g., immunoprecipitation, western blotting, etc.) using an anti-TREM-2 antibody and an anti-phosphorylated tyrosine antibody.

The ligand binding activity can be assayed by, e.g., immunoprecipitation, protein affinity purification, yeast two-hybrid techniques, etc., using the protein of the present invention (preferably TREM-2) and a ligand.

Examples of the protein used in the present invention include (1) so-called muteins such as proteins containing (i) the amino acid sequence represented by SEQ ID NO: 1, of which at least 1 or 2 (e.g., about 1 to about 100, preferably about 1 to about 30, more preferably about 1 to about 10 and most preferably several (1 to 5)) amino acids are deleted; (ii) the amino acid sequence represented by SEQ ID NO: 1, to which at least 1 or 2 (e.g., about 1 to about 100, preferably about 1 to about 30, more preferably about 1 to about 10 and most preferably several (1 to 5)) amino acids are added; (iii) the amino acid sequence represented by SEQ ID NO: 1, in which at least 1 or 2 (e.g., about 1 to about 100, preferably about 1 to about 30, more preferably about 1 to about 10 and most preferably several (1 to 5)) amino acids are inserted; (iv)

the amino acid sequence represented by SEQ ID NO: 1, in which at least 1 or 2 (e.g., about 1 to about 100, preferably about 1 to about 30, more preferably about 1 to about 10 and most preferably several (1 to 5)) amino acids are substituted by other amino acids; or (v) a combination of these amino acid sequences; and, (2) so-called muteins such as proteins containing (i) the amino acid sequence represented by SEQ ID NO: 2, of which at least 1 or 2 (e.g., about 1 to about 100, preferably about 1 to about 30, more preferably about 1 to about 10 and most preferably several (1 to 5)) amino acids are deleted; (ii) the amino acid sequence represented by SEQ ID NO: 2, to which at least 1 or 2 (e.g., about 1 to about 100, preferably about 1 to about 30, more preferably about 1 to about 10 and most preferably several (1 to 5)) amino acids are added; (iii) the amino acid sequence represented by SEQ ID NO: 2, in which at least 1 or 2 (e.g., about 1 to about 100, preferably about 1 to about 30, more preferably about 1 to about 10 and most preferably several (1 to 5)) amino acids are inserted; (iv) the amino acid sequence represented by SEQ ID NO: 2, in which at least 1 or 2 (e.g., about 1 to about 100, preferably about 1 to about 30, more preferably about 1 to about 10 and most preferably several (1 to 5)) amino acids are substituted by other amino acids; or (v) a combination of these amino acid sequences; etc.

Where an amino acid sequence(s) are inserted, deleted or substituted as described above, the positions of such insertion, deletion or substitution are not particularly limited.

Throughout the specification, the proteins are represented in accordance with the conventional way of describing proteins, that is, the N-terminus (amino terminus) at the left hand and the C-terminus (carboxyl terminus) at the right hand. In the protein of the present invention including the protein containing the amino acid sequence represented by SEQ ID NO: 1, the C-terminus may be in any form of a carboxyl group (—COOH), a carboxylate (—COO$^-$), an amide (—CONH$_2$) and an ester (—COOR).

Herein, examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; pivaloyloxymethyl and the like.

Where the protein used in the present invention contains a carboxyl group (or a carboxylate) at a position other than the C-terminus, the carboxyl group may be amidated or esterified and such an amide or ester is also included within the protein used in the present invention. Examples of the ester group in this case may be the C-terminal esters described above, etc.

Furthermore, examples of the protein used in the present invention include variants wherein the amino group at the N-terminal amino acid residues (e.g., methionine residue) is protected with a protecting group (e.g., a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins having sugar chains; etc.

Specific examples of the protein used in the present invention are a protein containing the amino acid sequence represented by SEQ ID NO: 1 (human TREM-2), a protein containing the amino acid sequence represented by SEQ ID NO: 2 (mouse TREM-2), and the like.

The partial peptide of the protein used in the present invention may be any peptide as long as it is a partial peptide of the protein used in the present invention described above and preferably has the property equivalent to that of the protein used in the present invention described above.

Specifically, for the purpose of preparing the antibody of the present invention later described, there are a peptide having the 133-147 amino acid sequence in the amino acid sequence represented by SEQ ID NO: 1, a peptide having the 133-147 amino acid sequence in the amino acid sequence represented by SEQ ID NO: 2, etc. Preferably used are peptides containing the sequence of, e.g., at least 20, preferably at least 50, more preferably at least 70, much more preferably at least 100, and most preferably at least 200, amino acids in the constituent amino acid sequence of the protein used the present invention, and the like.

The partial peptides used in the present invention may be peptides containing the amino acid sequence, of which at least 1 or 2 (preferably about 1 to about 10 and more preferably several (1 to 5)) amino acids may be deleted; peptides, to which at least 1 or 2 (preferably about 1 to about 20, more preferably about 1 to about 10 and most preferably several (1 to 5)) amino acids may be added; peptides, in which at least 1 or 2 (preferably about 1 to about 20, more preferably about 1 to about 10 and most preferably several (1 to 5)) amino acids may be inserted; or peptides, in which at least 1 or 2 (preferably about 1 to about 10, more preferably several and most preferably about 1 to about 5) amino acids may be substituted by other amino acids.

The partial peptides used in the present invention further include extracellular domains of the protein used in the present invention. The extracellular domains are, for example, a peptide having the 14-167 or 19-173 amino acid sequence in the amino acid sequence represented by SEQ ID NO: 1, a peptide having the 14-170 or 19-170 amino acid sequence in the amino acid sequence represented by SEQ ID NO: 2, and the like.

In the partial peptide of the present invention, the C-terminus may be in any form of a carboxyl group (—COOH), a carboxylate (—COO$^-$), an amide (—CONH$_2$) or an ester (—COOR).

Furthermore, the partial peptide used in the present invention includes variants having a carboxyl group (or a carboxylate) at a position other than the C-terminus, those wherein the amino group at the N-terminal amino acid residues (e.g., methionine residue) is protected with a protecting group; those wherein the N-terminal region is cleaved in vivo and the glutamyl group thus formed is pyroglutaminated; those wherein a substituent on the side chain of an amino acid in the molecule is protected with a suitable protecting group, or conjugated proteins such as so-called glycoproteins having sugar chains; etc., as in the protein of the present invention described above.

The partial peptide used in the present invention may also be used as an antigen for producing antibodies.

As salts of the protein or partial peptide used in the present invention, salts with physiologically acceptable acids (e.g., inorganic acids or organic acids) or bases (e.g., alkali metal salts) may be employed, preferably in the form of physiologically acceptable acid addition salts. Examples of such salts include salts with inorganic acids (e.g., hydrochloric acid, phosphoric acid, hydrobromic acid, and sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The protein or partial peptide used in the present invention or salts thereof may be manufactured by publicly known methods of purifying proteins from human or other warm-blooded animal cells or tissues described above. Alternatively, they may also be manufactured by culturing transformants containing DNAs encoding these proteins. Furthermore, they may also be manufactured by a modification of the methods for peptide synthesis, which will be described hereinafter.

Where these proteins are manufactured from human or mammalian tissues or cells, human or mammalian tissues or cells are homogenized, extracted with an acid, etc., and the extract can be isolated and purified by a combination of chromatography techniques such as reverse phase chromatography, ion exchange chromatography, and the like.

To synthesize the protein or partial peptide used in the present invention or its salts, or amides thereof, commercially available resins for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids, in which α-amino groups and functional groups on the side chains are appropriately protected, are condensed on the resin in the order of the sequence of the objective protein according to various condensation methods publicly known in the art. At the end of the reaction, the protein or partial peptide is excised from the resin and at the same time, the protecting groups are removed. Then, intramolecular disulfide bond-forming reaction is performed in a highly diluted solution to obtain the objective protein or partial peptide, or amides thereof.

For condensation of the protected amino acids described above, a variety of activation reagents for protein synthesis may be used, and carbodiimides are particularly preferred. Examples of such carbodiimides include DCC, N,N'-diisopropylcarbodiimide, N-ethyl-N'-(3-dimethylaminopropyl) carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents that are known to be usable for protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (linear, branched or cyclic alkyl esterification of, e.g., methyl, ethyl, propyl, butyl, t-butyl, cyclopentyl, cyclohexyl, cycloheptyl, cyclooctyl, 2-adamantyl, etc.), aralkyl esterification (e.g., benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group; tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting material include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)].

As the amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid, trifluoroacetic acid, or a mixture solution of these acids; a treatment with a base such as diisopropylethylamine, triethylamine, piperidine or piperazine; reduction with sodium in liquid ammonia, etc. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the desired protein or partial peptide, for example, the α-carboxyl group of the carboxy terminal amino acid is first protected by amidation; the peptide (protein) chain is then extended from the amino group side to a desired length. Then, a protein or partial peptide, in which only the protecting group of the N-terminal α-amino group of the peptide chain has been eliminated, and a protein or partial peptide, in which only the protecting group of the C-terminal carboxyl group has been eliminated are manufactured. The two proteins or peptides are condensed in a mixture of the solvents described above. The details of the condensation reaction are the same as described above. After the protected protein or peptide obtained by the condensation is purified, all the protecting groups are eliminated by the method described above to give the desired crude protein or peptide. This crude protein or peptide is purified by various known purification means. Lyophilization of the major fraction gives the amide of the desired protein or peptide.

To prepare the esterified protein or peptide, for example, the α-carboxyl group of the carboxy terminal amino acid is condensed with a desired alcohol to prepare the amino acid ester, which is followed by procedures similar to the preparation of the amidated protein or peptide above to give the desired esterified protein or peptide.

The partial peptide used in the present invention or salts thereof can be manufactured by publicly known methods for peptide synthesis, or by cleaving the protein used in the present invention with an appropriate peptidase. For the methods for peptide synthesis, for example, either solid phase synthesis or liquid phase synthesis may be used. That is, the partial peptide or amino acids that can construct the partial peptide used in the present invention are condensed with the remaining part. Where the product contains protecting groups, these protecting groups are removed to give the desired peptide. Publicly known methods for condensation and elimination of the protecting groups are described in (i) to (v) below.

(i) M. Bodanszky & M. A. Ondetti: Peptide Synthesis, Interscience Publishers, New York (1966)

(ii) Schroeder & Luebke: The Peptide, Academic Press, New York (1965)

(iii) Nobuo Izumiya, et al.: Peptide Gosei-no-Kiso to Jikken (Basics and experiments of peptide synthesis), published by Maruzen Co. (1975)

(iv) Haruaki Yajima & Shunpei Sakakibara: Seikagaku Jikken Koza (Biochemical Experiment) 1, Tanpakushitsu no Kagaku (Chemistry of Proteins) IV, 205 (1977)

(v) Haruaki Yajima ed.: Zoku Iyakuhin no Kaihatsu (A sequel to Development of Pharmaceuticals), Vol. 14, Peptide Synthesis, published by Hirokawa Shoten After completion of the reaction, the partial peptide used in the present invention may be purified and isolated by a combination of conventional purification methods such as solvent extraction, distillation, column chromatography, liquid chromatography and recrystallization to give the partial peptide of the present invention. When the partial peptide obtained by the above methods is in a free form, the partial peptide can be converted into an appropriate salt by a publicly known method; when the partial peptide is obtained in a salt form, it can be converted into a free form or other different salt form by a publicly known method.

The polynucleotide encoding the protein used in the present invention may be any polynucleotide so long as it contains the base sequence encoding the protein used in the present invention described above. Preferably, the polynucleotide is a DNA. The DNA may be any one of genomic DNA, genomic DNA library, cDNA derived from the cells and/or tissues described above, cDNA library derived from the cells and/or tissues described above and synthetic DNA.

The vector used for the library may be any of bacteriophage, plasmid, cosmid, phagemid and the like. In addition, the DNA can be amplified by reverse transcriptase polymerase chain reaction (hereinafter abbreviated as RT-PCR) with total RNA or mRNA fraction prepared from the above-described cells and/or tissues.

The DNA encoding the protein used in the present invention may be any one of a DNA having, for example, the base sequence represented by SEQ ID NO: 3, or any DNA having a base sequence hybridizable to the base sequence represented by SEQ ID NO: 3 under high stringent conditions and encoding a protein which has the properties substantially equivalent to those of the protein containing the amino acid sequence represented by SEQ ID NO: 1.

Specific examples of the DNA that is hybridizable to the base sequence represented by SEQ ID NO: 3 under high stringent conditions include DNAs containing the base sequence having at least about 60% homology, preferably at least about 70% homology, preferably at least about 80% homology, preferably at least about 90% homology and preferably at least about 95% homology, to the base sequence represented by SEQ ID NO: 4; etc.

The hybridization can be carried out by publicly known methods or by modifications thereof, for example, according to the method described in Molecular Cloning, 2nd ed. (J. Sambrook et al., Cold Spring Harbor Lab. Press, 1989). A commercially available library can also be used according to the instructions of the attached manufacturer's protocol. The hybridization can be carried out preferably under high stringent conditions.

The high stringent conditions are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

More specifically, as the DNA encoding the protein containing the amino acid sequence represented by SEQ ID NO: 1, there may be employed a DNA containing the base sequence represented by SEQ ID NO: 3. As the DNA encoding the protein containing the amino acid sequence represented by SEQ ID NO: 2, there may be employed a DNA containing the base sequence represented by SEQ ID NO: 4, etc.

The DNA encoding the partial peptide used in the present invention may be any DNA so long as it contains the base sequence encoding the partial peptide used in the present invention described above. The DNA may also be any of genomic DNA, genomic DNA library, cDNA derived from the cells and/or tissues described above, cDNA library derived from the cells and/or tissues described above and synthetic DNA.

As the DNA encoding the partial peptide used in the present invention, there are employed, for example, a DNA containing a part of DNA containing the base sequence represented by SEQ ID NO: 3, or a DNA containing a base sequence hybridizable to the base sequence represented by SEQ ID NO: 3 under high stringent conditions and containing a part of DNA encoding a protein having the activities substantially equivalent to those of the protein of the present invention; etc.

The DNA hybridizable to the base sequence represented by SEQ ID NO: 3 has the same significance as described above.

The DNA hybridizable to the base sequence represented by SEQ ID NO: 3 has the same significance as described above.

Methods for the hybridization and the high stringent conditions that can be used are the same as those described above.

For cloning of DNAs that completely encode the protein or partial peptide used in the present invention (hereinafter sometimes merely referred to as the protein of the present invention in the description of cloning of DNAs encoding the protein and partial peptide and their expression), the DNA can be either amplified by PCR using synthetic DNA primers containing a part of the base sequence of the protein of the present invention, or the DNA inserted into an appropriate vector can be screened by hybridization with a labeled DNA fragment or synthetic DNA that encodes a part or entire region of the protein of the present invention. The hybridization can be carried out, for example, according to the method described in Molecular Cloning, 2nd (J. Sambrook et al., Cold Spring Harbor Lab. Press, 1989). Where the hybridization is carried out using commercially available library, the procedures may be conducted in accordance with the protocol described in the attached instructions.

Conversion of the base sequence of DNA can be effected by publicly known methods such as PCR, the ODA-LA PCR method, the Gapped duplex method, the Kunkel method, etc., or its modification, using a publicly known kit available as Mutan™-super Express Km (manufactured by Takara Shuzo Co., Ltd.) or Mutan™-K (manufactured by Takara Shuzo Co., Ltd.), etc.

The cloned DNA encoding the protein can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector for the protein of the present invention can be manufactured, for example, by (a) excising the objective DNA fragment from the DNA encoding the protein of the present invention, and then (b) ligating the DNA fragment with an appropriate expression vector downstream a promoter in the vector.

Examples of the vector include plasmids derived form $E.$ $coli$ (e.g., pBR322, pBR325, pUC12, pUC13), plasmids derived from $Bacillus\ subtilis$ (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNA I/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, it is preferred to use CMV (cytomegalovirus) promoter, SRα promoter, etc. Where the host is bacteria of the genus $Escherichia$, preferred examples of the promoter include trp promoter, lac promoter, recA promoter, $\lambda P_L$ promoter, lpp promoter, T7 promoter, etc. In the case of using bacteria of the genus $Bacillus$ as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo$^r$, G418 resistance), etc. In particular, when dhfr gene is used as the selection marker using dhfr gene-deficient Chinese hamster cells, selection can also be made on a thymidine free medium.

If necessary, a signal sequence that matches with a host is added to the N-terminus of the protein of the present invention. Examples of the signal sequence that can be used are PhoA signal sequence, OmpA signal sequence, etc. when bacteria of the genus $Escherichia$ is used as the host; α-amylase signal sequence, subtilisin signal sequence, etc. when bacteria of the genus $Bacillus$ is used as the host; MFα signal sequence, SUC2 signal sequence, etc. when yeast is used as the host; and insulin signal sequence, α-interferon signal sequence, antibody molecule signal sequence, etc. when animal cells are used as the host, respectively.

Using the vector containing the DNA encoding the protein of the present invention thus constructed, transformants can be manufactured.

Examples of the host, which may be employed, are bacteria belonging to the genus $Escherichia$, bacteria belonging to the genus $Bacillus$, yeast, insect cells, insects and animal cells, etc.

Specific examples of the bacteria belonging to the genus $Escherichia$ include $Escherichia\ coli$ K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus $Bacillus$ include $Bacillus\ subtilis$ MI114 [Gene, 24, 255 (1983)], 207-21 [Journal of Biochemistry, 95, 87 (1984)], etc.

Examples of yeast include $Saccharomyces\ cereviseae$ AH22, AH22R$^-$, NA87-11A, DKD-5D, 20B-12, $Schizosaccharomyces\ pombe$ NCYC1913, NCYC2036, $Pichia\ pastoris$ KM71, etc.

Examples of insect cells include, for the virus AcNPV, $Spodoptera\ frugiperda$ cell (Sf cell), MG1 cell derived from mid-intestine of Trichoplusia ni, High Five™ cell derived from egg of $Trichoplusia\ ni$, cells derived from $Mamestra\ brassicae$, cells derived from $Estigmena\ acrea$, etc.; and for the virus BmNPV, $Bombyx\ mori$ N cell (BmN cell), etc. is used. Examples of the Sf cell which can be used are Sf9 cell (ATCC CRL1711), Sf21 cell (both cells are described in Vaughn, J. L. et al., In Vivo, 13, 213-217 (1977), etc.

As the insect, for example, a larva of $Bombyx\ mori$ can be used [Maeda et al., Nature, 315, 592 (1985)].

Examples of animal cells include monkey cell COS-7, Vero, Chinese hamster cell CHO (hereinafter referred to as CHO cell), dhfr gene-deficient Chinese hamster cell CHO (hereinafter simply referred to as CHO (dhfr$^-$) cell), mouse L cell, mouse AtT-20, mouse myeloma cell, mouse ATDC5 cell, rat GH3, human FL cell, 3T3-L1 cell, L6 cell, C2C12 cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55 (1988), etc.

Animal cells can be transformed, for example, according to the method described in Saibo Kogaku (Cell Engineering), extra issue 8, Shin Saibo Kogaku Jikken Protocol (New Cell Engineering Experimental Protocol), 263-267 (1995) (published by Shujunsha), or Virology, 52, 456 (1973).

Thus, the transformants transformed with the expression vectors containing the DNAs encoding the protein can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, and the like. Examples of the carbon sources include glucose, dextrin, soluble starch, sucrose, etc.; examples of the nitrogen sources include inorganic or organic materials such as ammonium salts, nitrate salts, corn steep liquor, peptone, casein, meat extract, soybean cake, potato extract, etc.; and, examples of the inorganic materials are calcium chloride, sodium dihydrogenphosphate, magnesium chloride, etc. In addition, yeast extracts, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431-433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15 to 43° C. for about 3 to 24 hours. If necessary, the culture may be aerated or agitated.

Where the bacteria belonging to the genus *Bacillus* are used as the host, the transformant is cultured generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, the pH of medium is adjusted to approximately 5 to 8. In general, the transformant is cultivated at approximately 20 to 35° C. for approximately 24 to 72 hours. If necessary, the culture can be aerated or agitated.

Where insect cells or insects are used as the host, the transformant is cultivated in, for example, Grace's Insect Medium (Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultured in, for example, MEM medium containing about 5 to 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 to about 60 hours and, if necessary, the culture can be aerated or agitated.

As described above, the protein of the present invention can be produced in the transformant, in the cell membrane of the transformant, or outside of the transformant.

The protein of the present invention can be separated and purified from the culture described above by the following procedures.

When the protein of the present invention is extracted from the bacteria or cells, the bacteria or cell is collected after culturing by a publicly known method and suspended in an appropriate buffer. The bacteria or cell is then disrupted by publicly known methods such as ultrasonication, a treatment with lysozyme and/or freeze-thaw cycling, followed by centrifugation, filtration, etc. to give the crude extract of the protein. These procedures are appropriately used. The buffer used for the procedures may contain a protein modifier such as urea or guanidine hydrochloride, or a surfactant such as Triton X-100™, etc. When the protein of the present invention is secreted in the culture broth, the supernatant can be separated, after completion of the cultivation, from the bacteria or cell to collect the supernatant by a publicly known method.

The protein contained in the supernatant or the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the protein thus obtained is in a free form, the protein can be converted into the salt by publicly known methods or modifications thereof. On the other hand, when the protein is obtained in the form of a salt, it can be converted into the free form or in the form of a different salt by publicly known methods or modifications thereof.

The protein produced by the recombinant can be treated, prior to or after the purification, with an appropriate protein-modifying enzyme so that the protein can be appropriately modified to partially remove the polypeptide. Examples of the protein-modifying enzyme include trypsin, chymotrypsin, arginyl endopeptidase, protein kinase, glycosidase and the like.

The presence of the thus produced protein of the present invention can be determined by an enzyme immunoassay or western blotting using a specific antibody.

The antibodies to the protein or partial peptide used in the present invention, or its salts may be any of polyclonal and monoclonal antibodies, as long as they are capable of recognizing the protein or partial peptide used in the present invention, or its salts.

The antibodies to the protein or partial peptide used in the present invention, or its salts, (hereinafter they are sometimes collectively referred to as the protein of the present invention in the description of the antibodies) can be produced by a publicly known method of producing an antibody or antiserum, using the protein of the present invention as an antigen.

[Preparation of Monoclonal Antibody]

(a) Preparation of Monoclonal Antibody-Producing Cells

The protein of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every about 2 to about 6 weeks and about 2 to about 10 times in total. Examples of the applicable warm-blooded animals are monkeys, rabbits, dogs, guinea pigs, mice, rats, sheep, goats and fowl, with the use of mice and rats being preferred.

In the preparation of monoclonal antibody-producing cells, warm-blooded animals, e.g., mice, immunized with an antigen wherein the antibody titer is noted are selected, then spleen or lymph node is collected after 2 to 5 days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled protein, which will be described later, with the antiserum followed by assaying the binding activity of the labeling agent bound to the antibody. The fusion may be carried out, for example, by the known method by Koehler and Milstein [Nature, 256, 495, (1975)]. Examples of the fusion accelerator are polyethylene glycol (PEG), Sendai virus, etc., among which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubation at 20 to 40° C., preferably at 30 to 37° C. for 1 to 10 minutes, an efficient cell fusion can be carried out.

Various methods can be used for screening of monoclonal antibody-producing hybridomas. Examples of such methods include a method which comprises adding the supernatant of a hybridoma to a solid phase (e.g., a microplate) adsorbed with the protein as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the protein labeled with a radioactive substance or an enzyme and detecting the monoclonal antibody bound to the solid phase, or the like.

The monoclonal antibody can be screened according to publicly known methods or their modifications. In general, the screening can be performed in a medium for animal cells supplemented with HAT (hypoxanthine, aminopterin and thymidine). Any screening and growth medium can be employed as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for cultivation of a hybridoma (SFM-101, Nissui Seiyaku Co., Ltd.) and the like, can be used for the screening and growth medium. The culture is carried out generally at 20 to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody.]

[Preparation of Polyclonal Antibody]

The polyclonal antibody of the present invention can be manufactured by publicly known methods or modifications thereof. For example, a warm-blooded animal is immunized with an immunogen (protein antigen) per se, or a complex of immunogen and a carrier protein is formed and a warm-blooded animal is immunized with the complex in a manner similar to the method described above for the manufacture of monoclonal antibodies. The product containing the antibody to the protein of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or hemocyanin is coupled to hapten in a carrier-to-hapten weight ratio of approximately 0.1 to 20, preferably approximately 1 to 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to a warm-blooded animal either solely or together with carriers or diluents to the site that can produce the antibody by the administration. In order to potentiate the antibody productivity upon the administration, complete Freund's adjuvant or incomplete Freund's adjuvant may be administered. The administration is usually made once every about 2 to 6 weeks and about 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The antisense polynucleotide having a complementary or substantially complementary base sequence to the DNA encoding the protein or partial peptide used in the present invention (hereinafter these DNAs are sometimes collectively referred to as the DNA of the present invention in the description of antisense polynucleotide) can be any antisense polynucleotide, so long as it possesses a base sequence complementary or substantially complementary base sequence to that of the DNA of the present invention and capable of suppressing expression of the DNA, but antisense DNA is preferred.

The base sequence substantially complementary to the DNA of the present invention may include, for example, a base sequence having at least about 70% homology, preferably at least about 80% homology, more preferably at least about 90% homology and most preferably at least about 95% homology, to the entire base sequence or the partial base sequence of the base sequence complementary to the DNA of the present invention (i.e., complementary strand to the DNA of the present invention), and the like. Especially in the entire base sequence of the complementary strand to the DNA of the present invention, (a) in the case of antisense polynucleotide directed to translation inhibition, an antisense polynucleotide having at least about 70% homology, preferably at least about 80% homology, more preferably at least about 90% homology and most preferably at least about 95% homology, to the complementary strand of the base sequence, which encodes the N-terminal region of the protein of the present invention (e.g., the base sequence around the initiation codon, etc.), (b) in the case of antisense polynucleotide directed to RNA cleavage by RNaseH, an antisense polynucleotide having at least about 70% homology, preferably at least about 80% homology, more preferably at least about 90% homology and most preferably at least about 95% homology, to the complementary strand of the entire base sequence of the DNA of the present invention containing introns, are suitable, respectively.

Specifically, there are an antisense polynucleotide containing the entire or part of a complementary or substantially complementary base sequence to a base sequence of DNA containing the base sequence represented by SEQ ID NO: 3 or SEQ ID NO: 4, preferably an antisense polynucleotide containing the entire or part of a complementary base sequence to a base sequence of DNA containing the base sequence represented by SEQ ID NO: 3 or SEQ ID NO: 4 (more preferably, an antisense polynucleotide containing the entire or part of a complementary base sequence to a base sequence of DNA containing the base sequence represented by SEQ ID NO: 3, or an antisense polynucleotide containing the entire or part of a complementary base sequence to a base sequence of DNA containing the base sequence represented by SEQ ID NO: 4).

The antisense polynucleotide is generally constituted by bases of about 10 to about 40, preferably about 15 to about 30.

To prevent digestion with a hydrolase such as nuclease, etc., the phosphoric acid residue (phosphate) of each nucleotide that constitutes the antisense DNA may be substituted with chemically modified phosphoric acid residues, e.g., phosphorothioate, methyl phosphonate, phosphorodithionate, etc. Also, the sugar (deoxyribose) in each nucleotide may be replaced by a chemically modified structure such as 2'-O-methylation, etc. The base part (pyrimidine, purine) may also be chemically modified and may be any one which hybridizes to a DNA containing the base sequence represented by SEQ ID NO: 2. These antisense nucleotides may be synthesized using a publicly known DNA synthesizer, etc. According to the present invention, the antisense polynucleotide (nucleic acid) capable of inhibiting the replication or expression of a gene for the protein of the present invention can be designed and synthesized based on the base sequence information of cloned or identified protein-encoding DNA. Such a polynucleotide (nucleic acid) is hybridizable to RNA of the protein gene of the present invention to inhibit the synthesis or function of said RNA or is capable of modulating and/or controlling the expression of the protein gene of the present invention via interaction with RNA associated with the protein of the present invention. Polynucleotides complementary to the selected sequences of RNA associated with the protein of the present invention and polynucleotides specifically hybridizable to RNA associated with the protein of the present invention are useful in modulating and/or controlling the in vivo and in vitro expression of the protein gene of the present invention, and are useful for the treatment or diagnosis of diseases, etc. The term "corresponding" is used to mean homologous to or complementary to a particular sequence of the nucleotide including the gene, base sequence or nucleic acid. The term "corresponding" between nucleotides, base sequences or nucleic acids and peptides (proteins) usually refer to amino acids of a peptide (protein) under the order derived from the sequence of nucleotides (nucleic acids) or their complements. In the protein genes, the 5' end hairpin loop, 5' end 6-base-pair repeats, 5' end untranslated region, polypeptide translation initiation codon, protein coding region, ORF translation termination codon, 3' end untranslated region, 3' end palindrome region, and 3' end hairpin loop, may be selected as preferred target regions, though any other region may be selected as a target in the protein genes.

The relationship between the targeted nucleic acids and the polynucleotides complementary to at least a part of the target region, or the relationship between the target and the hybridizable polynucleotide can be denoted to be "antisense." Examples of the antisense polynucleotides include polynucleotides containing 2-deoxy-D-ribose, polynucleotides containing D-ribose, any other type of polynucleotides which are N-glycosides of a purine or pyrimidine base, or other polymers containing non-nucleotide backbones (e.g., commercially available protein nucleic acids and synthetic sequence-specific nucleic acid polymers) or other polymers containing nonstandard linkages (provided that the polymers contain nucleotides having such a configuration that allows base pairing or base stacking, as is found in DNA or RNA), etc. The antisense polynucleotides may be double-stranded DNA, single-stranded DNA, double-stranded RNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., a anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfur and thiophosphate derivatives of nucleic acids and those resistant to degradation of polynucleoside amides or oligonucleoside amides. The antisense nucleic acids of the present invention can be modified preferably based on the following design, that is, by increasing the intracellular stability of the antisense nucleic acid, increasing the cell permeability of the antisense nucleic acid, increasing the affinity of the nucleic acid to the targeted sense strand to a higher level, or minimizing the toxicity, if any, of the antisense nucleic acid.

Many of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense nucleic acid of the present invention may contain altered or modified sugars, bases or linkages. The antisense nucleic acid may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleic acid can be examined using the transformant of the present invention, the gene expression system of the present invention in vivo and in vitro, or the translation system of the protein in vivo and in vitro. The nucleic acid can be applied to cells by a variety of publicly known methods.

Hereinafter, the protein of the present invention, its partial peptides, or salts thereof (hereinafter sometimes merely referred to as the protein of the present invention), the DNA encoding the protein of the present invention or its partial peptides (hereinafter sometimes merely referred to as the DNA of the present invention), the antibodies to the protein of the present invention, its partial peptides, or salts thereof (hereinafter sometimes referred to as the antibodies of the present invention) and the antisense polynucleotides to the DNA of the present invention (hereinafter sometimes merely referred to as the antisense polynucleotides of the present invention) are specifically described for their applications.

The protein of the present invention can be utilized as a disease marker since expression of the protein increases in adipose tissues. That is, the protein is useful as a marker for early diagnosis in insulin resistance, judgment of severity in conditions, or predicted development of disease. Furthermore, the protein of the present invention has an effect of inducing or aggravating insulin resistance to increase blood glucose and blood fat levels. Therefore, pharmaceuticals which comprises the antisense polynucleotide of the present invention, the compound or its salt that inhibits the expression of the protein gene of the present invention or the antibody of the present invention can be used, for example, as insulin-sensitizing agents, or further as agents for the prevention and/or treatment of diabetes, obesity, hyperlipemia, arteriosclerosis, hypertension or heart disease.

(1) Screening of Drug Candidate Compounds for Disease

Since expression of the protein of the present invention increases in adipose tissues, the protein has an effect of inducing or aggravating insulin resistance and increases blood glucose and blood fat. Thus, the compound or its salt that inhibits the activity of the protein of the present invention can be used, for example, as insulin-sensitizing agents, or as pharmaceuticals for the prevention and/or treatment of diabetes, obesity, hyperlipemia, arteriosclerosis, hypertension or heart disease.

Therefore, the protein of the present invention is useful as a reagent for screening the compound or its salt that inhibits the activity of the protein of the present invention.

That is, the present invention provides a method of screening the compound or its salt that inhibits the activity (e.g., a ligand binding activity, a signal transduction activity, etc.) of the protein of the present invention, which comprises using the protein of the present invention.

More specifically, there is employed a method of screening the compound or its salt that inhibits the activity of the protein of the present invention, which comprises comparing, for example, (i) the ligand binding activity or signal transduction activity of a cell capable of producing the protein of the present invention and (ii) the ligand binding activity or signal transduction activity of a cell capable of producing the protein of the present invention in the presence of a test compound.

In the screening method described above, for example, in the cases of (i) and (ii), the ligand binding activity or signal transduction activity can be assayed by publicly known techniques, e.g., by the technique described in J. Exp. Med., 194, 1111-1122, 2001, or with modifications of the technique, and comparison is made.

Specifically, (1) the level of phosphorylated ERK produced, (2) the level of TNF-α produced and secreted extracellularly or (3) the level of phosphorylated protein of the present invention (preferably phosphorylated TREM-2) produced is determined, respectively, (i) in the case that a cell (e.g., an animal cell) overexpressed with the protein of the present invention wherein a vector expressing the protein of the present invention has been introduced is cultured, if required by adding to the cell (a) a ligand-containing fluid such as a microorganism lysate, a microorganism supernatant, an eukaryotic cell lysate, an eukaryotic cell supernatant, etc., (b) a ligand itself, (c) a substance having a binding activity to the protein of the present invention equivalent to a naturally occurring ligand or (d) an antibody activating the protein of the present invention (e.g., TREM-2) and (ii) in the case that a cell (e.g., an animal cell) overexpressed with the protein of the present invention wherein a vector expressing the protein of the present invention has been introduced is cultured in the presence of a test compound, if required by adding to the cell (a) a ligand-containing fluid such as a microorganism lysate, a microorganism supernatant, an eukaryotic cell lysate, an eukaryotic cell supernatant, etc., (b) a ligand itself, (c) a substance having a binding activity to the protein of the present invention equivalent to a naturally occurring ligand or (d) an antibody activating the protein of the present invention (e.g., TREM-2), followed by comparison.

The aforesaid level of phosphorylated ERK or the level of TNF-α produced can be assayed by publicly known methods (e.g., western blotting, EIA, etc.) using an anti-phosphorylated ERK antibody or an anti-TNF-α antibody. The level of phosphorylated TREM-2 produced can be assayed by publicly known methods (e.g., immunoprecipitation, western blotting, etc.) using an anti-TREM-2 antibody and an anti-phosphorylated tyrosine antibody.

As the cells capable of producing the protein of the present invention, there are used, for example, hosts transformed by a vector containing a DNA encoding the protein of the present invention described above (transformants). As the hosts, animal cells such as COS-7 cells, CHO cells, HEK293 cells, 3T3-L1 cells, L6 cells, C2C12 cells, etc. are preferably used. For the screening, transformants with the protein of the present invention expressed on the cell membrane through incubation by the techniques described above are preferably employed. The techniques for incubation of the cell capable of expressing the protein of the present invention are the same as the techniques for incubation of the transformants of the present invention described above.

Examples of the test compound include peptides, proteins, non-peptide compounds, synthetic compounds, fermentation products, cell extracts, plant extracts, animal tissue extracts, etc.

For example, when a test compound reduces the ligand binding activity or the signal transduction activity in the case (i) described above at least by about 20%, preferably at least by about 30%, more preferably at least by about 50%, as compared to the case (ii) above, the test compound can be selected to be a compound capable of inhibiting the activity of the protein of the present invention.

The compound having the activity of inhibiting the activity of the protein of the present invention is useful as a safe and low toxic pharmaceutical for suppressing the physiological activity of the protein of the present invention.

The compound or its salt obtained using the screening method or screening kit of the present invention is a compound selected from, for example, peptides, proteins, non-peptide compounds, synthetic compounds, fermentation products, cell extracts, plant extracts, animal tissue extracts, plasma, etc. The salts of the compound used are those given above as the salts of the peptide of the present invention.

Furthermore, expression of the gene encoding the protein of the present invention also increases in adipose tissues and thus, the compound or its salt that inhibits expression of the gene encoding the protein of the present invention can be used as, e.g., an insulin-sensitizing agent, or an agent for the prevention and/or treatment of diabetes, obesity, hyperlipemia, arteriosclerosis, hypertension or heart disease, and so on.

Accordingly, the DNA of the present invention is useful as a reagent for screening the compound or its salt that inhibits expression of the gene encoding the protein of the present invention.

For the screening method, there is a method of screening, which comprises comparing (iii) the case in which the cell capable of producing the protein of the present invention is incubated and (iv) the case in which the cell capable of producing the protein used in the present invention is incubated in the presence of a test compound.

In the method described above, the level of the aforesaid gene expressed (specifically, the level of the protein of the present invention or the level of mRNA encoding the protein) is measured in the cases (iii) and (iv), and comparison is made therebetween.

As the test compound and the cell capable of producing the protein of the present invention, the same examples as described above are given.

The level of the protein can be determined by publicly known methods, e.g., by measuring the aforesaid protein present in the cell extract, etc., using an antibody capable of recognizing the protein of the present invention, in accordance with techniques such as western blotting, EIA, etc., or their modifications.

The level of mRNA can be determined by publicly known techniques, e.g., Northern hybridization, RT-PCR, or modifications thereof. Alternatively, a reporter gene (e.g., β-galactosidase, etc.) is ligated to a promoter of the gene for the protein of the present invention, the resulting vector is introduced into a cell (e.g., an animal cell, etc.), and the level of the reporter gene expressed may be determined.

For example, when a test compound inhibits the level of the gene expressed in the case (iv) described above at least by about 20%, preferably at least by about 30%, more preferably at least by about 50%, as compared to the case (iii) above, the test compound can be selected to be a compound capable of inhibiting the expression of the gene encoding the protein of the present invention.

The screening kit of the present invention comprises the protein used in the present invention, its partial peptide, or a salt thereof, or the cell capable of producing the protein used in the present invention, or its partial peptide.

The compound or its salt obtained using the screening method or screening kit of the present invention is a compound or its salt selected from the test compounds described above, for example, peptides, proteins, non-peptide compounds, synthetic compounds, fermentation products, cell extracts, plant extracts, animal tissue extracts, plasma, etc., and is a compound or its salt, which regulates the activity (e.g., the ligand binding activity, the signal transduction activity, etc.) of the protein of the present invention.

Examples of the salt of the compound are the same as those salts given for the protein of the present invention described above.

The compound or its salt that inhibits the activity of the protein of the present invention and the compound or its salt that inhibits the expression of the gene encoding the protein of the present invention are respectively useful as pharmaceuticals such as insulin-sensitizing agents, agents for the prevention and/or treatment of diabetes, obesity, hyperlipemia, arteriosclerosis, hypertension or heart disease, and so on.

Where the compound or its salt obtained using the screening method or screening kit of the present invention is used as the agent for the prevention and/or treatment described above, the compound or its salt can be prepared into a pharmaceutical composition in a conventional manner.

For example, the composition for oral administration includes solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, etc.

Examples of the composition for parenteral administration are injectable preparations, suppositories, etc. The injectable preparations may include dosage forms such as intravenous injection, subcutaneous injection, intracutaneous injection, intramuscular injection, drip infusion, intraarticular injection, etc. These injectable preparations may be prepared by methods publicly known in the art. For example, the injectable preparations may be prepared by dissolving, suspending or emulsifying the compound or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate dissolution aid such as an alcohol (e.g., ethanol), a polyalcohol (e.g., propylene glycol, polyethylene glycol), a nonionic surfactant [e.g., polysorbate 80, HCO-50 (polyoxyethylene (50 mols) adduct of hydrogenated castor oil)], etc. As the oily medium, there are employed, e.g., sesame oil, soybean oil, etc., which may be used in combination with a dissolution aid such as benzyl benzoate, benzyl alcohol, etc. The injectable preparation thus prepared is preferably filled in an appropriate ampoule. The suppository used for rectal administration may be prepared by blending the aforesaid compound or its salt with conventional bases for suppositories.

Advantageously, the pharmaceutical compositions for oral or parenteral use described above are prepared into pharmaceutical preparations with a unit dose suited to fit a dose of the active ingredients. Such unit dose preparations include, for example, tablets, pills, capsules, injections (ampoules), suppositories, etc. The amount of the aforesaid compound contained is generally 1 to 500 mg per each dosage unit form; especially in the form of injection, it is preferred that the aforesaid compound is contained in approximately 0.5 to 100 mg.

Each composition described above may further contain other active components, unless formulation with the compound described above causes any adverse interaction.

Since the pharmaceutical preparations thus obtained are safe and low toxic, they can be administered to, e.g., human or a warm-blooded animal (e.g., mouse, rat, rabbit, sheep, swine, bovine, horse, fowl, cat, dog, monkey, chimpanzee, etc.) orally or parenterally.

The dose of the compound or its salt may vary depending upon its action, target disease, subject to be administered, route of administration, etc. For example, when the compound or its salt that inhibits the activity of the protein of the present invention is orally administered for the purpose of sensitizing insulin, the compound or its salt is generally administered to an adult (as 60 kg body weight) in a daily dose of about 0.1 to about 100 mg, preferably about 1.0 to about 50 mg and more preferably about 1.0 to about 20 mg. In parenteral administration, a single dose of the said compound or its salt may vary depending upon subject to be administered, target disease, etc. When the compound or its salt that inhibits the activity of the protein of the present invention is administered to an adult (as 60 kg body weight) in the form of an injectable preparation for the purpose of sensitizing insulin, it is advantageous to administer the compound or its salt intravenously in a daily dose of about 0.01 to about 30 mg, preferably about 0.1 to about 20 mg, and more preferably about 0.1 to about 10 mg. For other animal species, the corresponding dose as converted per 60 kg weight can be administered.

(2) Quantification for the Protein of the Present Invention, it Partial Peptide or Salts Thereof.

The antibody to the protein of the present invention (hereinafter sometimes merely referred to as the antibody of the present invention) is capable of specifically recognizing the protein of the present invention, and thus can be used for quantification of the protein of the present invention in a test sample fluid, in particular, for quantification by sandwich immunoassay; etc.

That is, the present invention provides:

(i) a method for quantification of the protein of the present invention in a test sample fluid, which comprises competitively reacting the antibody of the present invention, a test sample fluid and the labeled form of the protein of the present invention, and measuring the ratio of the labeled form of the protein of the present invention bound to said antibody; and, (ii) a method for quantification of the protein of the present invention in a test sample fluid, which comprises reacting a test sample fluid simultaneously or continuously with the antibody of the present invention immobilized on a carrier and another labeled antibody of the present invention, and then measuring the activity of the labeling agent on the insoluble carrier.

In the quantification method (ii) described above, it is preferred that one antibody is capable of recognizing the N-terminal region of the protein of the present invention, while another antibody is capable of reacting with the C-terminal region of the protein of the present invention.

The monoclonal antibody to the protein of the present invention (hereinafter sometimes referred to as the monoclonal antibody of the present invention) can be used to quantify the protein of the present invention. In addition, the protein can be detected by means of a tissue staining as well. For these purposes, the antibody molecule per se may be used or $F(ab')_2$, Fab' or Fab fractions of the antibody molecule may also be used.

The method for quantification of the protein of the present invention using the antibody of the present invention is not particularly limited. Any quantification method can be used, so long as the amount of antibody, antigen or antibody-antigen complex corresponding to the amount of antigen (e.g., the amount of the protein) in a test sample fluid can be detected by chemical or physical means and the amount of the antigen can be calculated from a standard curve prepared from standard solutions containing known amounts of the antigen. For such an assay method, for example, nephrometry, the competitive method, the immunometric method, the sandwich method, etc. are suitably used and in terms of sensitivity and specificity, it is particularly preferred to use the sandwich method described hereinafter.

Examples of the labeling agent used in the assay method using the labeling substance are radioisotopes, enzymes, fluorescent substances, luminescent substances, and the like. As the radioisotopes, there are used, e.g., [$^{125}$I], [$^{131}$I], [$^{3}$H], [$^{14}$C], etc. The enzymes described above are preferably enzymes, which are stable and have a high specific activity, and include, e.g., β-galactosidase, β-glucosidase, an alkaline phosphatase, a peroxidase, malate dehydrogenase, etc. As the fluorescent substances, there are used, e.g., fluorescamine, fluorescein isothiocyanate, etc. As the luminescent substances described above there are used, e.g., luminol, a luminol derivative, luciferin, lucigenin, etc. Furthermore, the biotin-avidin system may be used as well for binding of an antibody or antigen to a labeling agent.

For immobilization of the antigen or antibody, physical adsorption may be used. Chemical binding techniques conventionally used for insolubilization or immobilization of proteins, enzymes, etc. may also be used. For carriers, there are used, e.g., insoluble polysaccharides such as agarose, dextran, cellulose, etc.; synthetic resin such as polystyrene, polyacrylamide, silicon, etc., and glass or the like.

In the sandwich method, the immobilized monoclonal antibody of the present invention is reacted with a test sample fluid (primary reaction), then with a labeled form of another monoclonal antibody of the present invention (secondary reaction), and the activity of the label on the immobilizing carrier is measured, whereby the amount of the protein of the present invention in the test sample fluid can be quantified. The order of the primary and secondary reactions may be reversed, and the reactions may be performed simultaneously or with an interval. The methods of labeling and immobilization can be performed by the methods described above. In the immunoassay by the sandwich method, the antibody used for immobilized or labeled antibodies is not necessarily one species, but a mixture of two or more species of antibody may be used to increase the measurement sensitivity.

In the methods of determining the protein of the present invention by the sandwich method, antibodies that bind to different sites of the protein of the present invention are preferably used as the monoclonal antibodies of the present invention used for the primary and secondary reactions. That is, in the antibodies used for the primary and secondary reactions are, for example, when the antibody used in the secondary reaction recognizes the C-terminal region of the protein of the present invention, it is preferable to use the antibody recognizing the region other than the C-terminal region for the primary reaction, e.g., the antibody recognizing the N-terminal region.

The monoclonal antibodies of the present invention can be used for the assay systems other than the sandwich method, for example, the competitive method, the immunometric method, nephrometry, etc.

In the competitive method, antigen in a test sample fluid and the labeled antigen are competitively reacted with antibody, and the unreacted labeled antigen (F) and the labeled antigen bound to the antibody (B) are separated (B/F separation). The amount of the label in B or F is measured, and the amount of the antigen in the test sample fluid is quantified. This reaction method includes a liquid phase method using a soluble antibody as an antibody, polyethylene glycol for B/F separation and a secondary antibody to the soluble antibody, and an immobilized method either using an immobilized antibody as the primary antibody, or using a soluble antibody as the primary antibody and immobilized antibody as the secondary antibody.

In the immunometric method, antigen in a test sample fluid and immobilized antigen are competitively reacted with a definite amount of labeled antibody, the immobilized phase is separated from the liquid phase, or antigen in a test sample fluid and an excess amount of labeled antibody are reacted, immobilized antigen is then added to bind the unreacted labeled antibody to the immobilized phase, and the immobilized phase is separated from the liquid phase. Then, the amount of the label in either phase is measured to quantify the antigen in the test sample fluid.

In the nephrometry, insoluble precipitate produced after the antigen-antibody reaction in gel or solution is quantified. When the amount of antigen in the test fluid is small and only a small amount of precipitate is obtained, laser nephrometry using scattering of laser is advantageously employed.

For applying these immunological methods to the measurement methods of the present invention, any particular conditions or procedures are not required. Systems for measuring the protein of the present invention or its salts are constructed by adding the usual technical consideration in the art to the conventional conditions and procedures. For the details of these general technical means, reference can be made to the following reviews and texts.

For example, Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immunoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd. ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies)) (all published by Academic Press Publishing).

As described above, the protein of the present invention can be quantified with high sensitivity, using the antibody of the present invention.

Furthermore, when an increased level or decreased level of the protein of the present invention is detected by quantifying the level of the protein of the present invention using the antibody of the present invention, it can be diagnosed that one suffers from insulin resistance, diabetes, obesity, hyperlipemia, arteriosclerosis, hypertension or heart disease, etc., or it is highly likely to suffer from these disease in the future.

Moreover, the antibody of the present invention can be used to detect the protein of the present invention, which is present in a test sample fluid such as a body fluid, a tissue, etc. The antibody can also be used to prepare an antibody column for purification of the protein of the present invention, detect the protein of the present invention in each fraction upon purification, analyze the behavior of the protein of the present invention in the cells under investigation; etc.

(3) Gene Diagnostic Agent

By using the DNA of the present invention, e.g., as a probe, an abnormality (gene abnormality) of the DNA or mRNA encoding the protein of the present invention in human or warm-blooded animal (e.g., rat, mouse, guinea pig, rabbit, fowl, sheep, swine, bovine, horse, cat, dog, monkey, chimpanzee, etc.) can be detected. Thus, the DNA of the present invention is useful as a gene diagnostic agent for detecting damages to the DNA or mRNA, its mutation, or decreased expression, increased expression, overexpression, etc. of the DNA or mRNA, and so on.

The gene diagnosis described above using the DNA of the present invention can be performed by, for example, the Northern hybridization publicly known in the art or the PCR-SSCP assay (Genomics, 5, 874-879, 1989, Proceedings of the National Academy of Sciences of the United States of America, 86, 2766-2770, 1989), etc.

For example, when overexpression or decreased expression is detected by Northern hybridization or DNA mutation is detected by the PCR-SSCP assay, it can be diagnosed that it is highly likely to suffer from, e.g., diabetes, obesity, hyperlipemia, arteriosclerosis, hypertension or heart disease, and so on.

(4) Pharmaceutical which Comprises the Extracellular Domain of the Protein of the Present Invention or its Salt The extracellular domain of the protein of the present invention or its salt has the activity of binding to the ligand of the protein of the present invention but has no signal transduction activity, and can thus suppress signal transduction of the protein of the present invention as a dominant negative protein. The extracellular domain of the protein of the present invention or its salt has an effect of sensitizing insulin to reduce blood glucose and blood fat.

Therefore, the extracellular domain of the protein of the present invention or its salt is useful as, e.g., an insulin-sensitizing agent and further as a pharmaceutical such as an agent for the prevention and/or treatment of diabetes, obesity, hyperlipemia, arteriosclerosis, hypertension or heart disease, and so on.

The extracellular domain of the protein of the present invention may be administered singly as it is, or as an appropriate pharmaceutical composition. The pharmaceutical composition used for the administration comprises the aforesaid extracellular domain or its salt and a pharmacologically acceptable carrier, a diluent or excipient. Such a composition is provided as a pharmaceutical composition suitable for oral or parenteral administration (e.g., subcutaneous administration).

The extracellular domain described above can be used orally, for example, in the form of tablets which may be sugar coated if necessary, capsules, elixirs, microcapsules, etc., or parenterally in the form of injectable preparations such as a sterile solution, a suspension, etc. in water or with other pharmaceutically acceptable liquid. These preparations can be prepared by mixing the polypeptide of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives which can be blended with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil or cherry. When the unit dosage is in the form of capsules, liquid carriers such as oils and fats may further be used together with the additives described above. A sterile composition for injection may be formulated by conventional procedures used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol, polyethylene glycol, etc.), a nonionic surfactant (e.g., polysorbate 80™, HCO-50, etc.), etc. Examples of the oily medium include sesame oil and soybean oil, which may also be used in combination with a dissolution aid such as benzyl benzoate, benzyl alcohol, etc. The pharmaceuticals may also be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

As the pharmaceutical preparation described above is low toxic, it can be administered to human or a mammal (e.g., rat, rabbit, sheep, swine, bovine, cat, dog, monkey, etc.) orally or parenterally (e.g., subcutaneously), directly as a liquid preparation or as a pharmaceutical composition in an appropriate dosage form. The dose may vary depending upon subject to be administered, target disease, condition, route of administration, etc. For example, when the pharmaceutical is used for the purpose of improving adult insulin resistance, it is advantageous to administer the domain described above as an injectable preparation in a single dose of about 0.01 to about 20 mg/kg body weight, preferably about 0.1 to about 10 mg/kg body weight, more preferably about 0.1 to about 5 mg/kg body weight, in about 1 to about 5 times per day, preferably in about 1 to about 3 times per day. In other parenteral administration and oral administration, the domain can be administered in a dose corresponding to the above dose. When the condition is especially severe, the dose may be increased according to the condition.

(5) Pharmaceutical which Comprises an Antisense Polynucleotide

The antisense polynucleotide of the present invention that binds to the DNA of the present invention complementarily to inhibit expression of the DNA is low toxic and can suppress the function (e.g., the ligand binding activity or the signal transduction activity) of the protein of the present invention or the DNA of the present invention in vivo. The antisense polynucleotide of the present invention has the action of sensitizing insulin to reduce blood glucose and blood fat.

Therefore, the antisense polynucleotide of the present invention can be used as an insulin-sensitizing agent and further as an agent for the prevention and/or treatment of obesity, hyperlipemia, arteriosclerosis, hypertension or heart disease, etc.

Where the above antisense polynucleotide is used as the agent for the prevention and/or treatment described above, it can be prepared into pharmaceutical preparations by publicly known techniques, which are provided for administration.

For example, the above antisense polynucleotide is administered directly, or the antisense polynucleotide is inserted into an appropriate vector such as retrovirus vector, adenovirus vector, adenovirus-associated virus vector, etc., followed by treating in a conventional manner. The antisense polynucleotide may then be administered orally or parenterally to human or mammal (e.g., rat, rabbit, sheep, swine, bovine, cat, dog, monkey, etc.) in a conventional manner. The antisense polynucleotide may also be administered directly as it stands, or may be prepared in pharmaceutical preparations together with a physiologically acceptable carrier to assist its uptake, which are then administered by gene gun or through a catheter such as a catheter with a hydrogel. Alternatively, the antisense polynucleotide may be prepared into an aerosol, which is topically administered into the trachea as an inhaler.

Further for purposes of improving pharmacokinetics, prolonging a half-life and improving intracellular uptake efficiency, the antisense polynucleotide described above is prepared into pharmaceutical preparations (injectable preparations) alone or together with a carrier such as liposome, etc. and the preparations may be administered intravenously, subcutaneously, intraarticularly, etc.

A dose of the antisense polynucleotide may vary depending on target disease, subject to be administered, route for administration, etc. For example, where the antisense polynucleotide of the present invention is administered for the purpose of sensitizing insulin, the antisense polynucleotide is generally administered to an adult (60 kg body weight) in a daily dose of about 0.1 to 100 mg.

In addition, the antisense polynucleotide may also be used as an oligonucleotide probe for diagnosis to examine the presence of the DNA of the present invention in tissues or cells and states of its expression.

As the antisense polynucleotide described above can, the double-stranded RNA containing a part of RNA encoding the protein of the present invention, ribozyme containing a part of RNA encoding the protein of the present invention, etc. can also prevent expression of the gene of the present invention to suppress the in vivo function of the protein used in the present invention or the DNA used in the present invention and thus can be used as, e.g., an insulin-sensitizing agent, an agent for the prevention and/or treatment of obesity, hyperlipemia, arteriosclerosis, hypertension or heart disease, etc.

The double-stranded RNA can be designed based on a sequence of the polynucleotide of the present invention and manufactured by modifications of publicly known methods (e.g., Nature, 411, 494, 2001).

The ribozyme can be designed based on a sequence of the polynucleotide of the present invention and manufactured by modifications of publicly known methods (e.g., TRENDS in Molecular Medicine, 7, 221, 2001). For example, the ribozyme can be manufactured by ligating a publicly known ribozyme to a part of the RNA encoding the protein of the present invention. A part of the RNA encoding the protein of the present invention includes a portion proximal to a cleavage site on the RNA of the present invention, which may be cleaved by a publicly known ribozyme (RNA fragment).

Where the double-stranded RNA or ribozyme described above is used as the agent for prevention and/or treatment described above, the double-stranded RNA or ribozyme is prepared into pharmaceutical preparations as in the antisense polynucleotide, and the preparations can be provided for administration.

(6) Pharmaceutical which Comprises the Antibody of the Present Invention

The antibody having the action of neutralizing the activity of the protein of the present invention has the action of sensitizing insulin to reduce blood glucose and blood fat.

Therefore, the antibody (preferably, neutralizing antibody) of the present invention can be used as, e.g., an insulin-sensitizing agent, or further as a pharmaceutical such as an agent for the prevention and/or treatment of obesity, hyperlipemia, arteriosclerosis, hypertension or heart disease, etc.

As the aforesaid pharmaceutical containing the antibody of the present invention is low toxic, the pharmaceutical can be administered to human or mammals (e.g., rats, rabbits, sheep, swine, bovine, cats, dogs, monkeys, etc.) orally or parenterally (e.g., intravenously), directly in the form of a liquid preparation, or as a pharmaceutical composition in an appropriate dosage form. The dose may vary depending upon subject to be administered, target disease, condition, route of administration, etc. For example, when the pharmaceutical preparation is used for the purpose of improving adult insulin resistance, it is advantageous to administer the antibody of the present invention as powder inhalation in a single dose of about 0.01 to about 20 mg/kg body weight, preferably about 0.1 to about 10 mg/kg body weight, more preferably about 0.1 to about 5 mg/kg body weight, in about 1 to about 5 times per day, preferably in about 1 to about 3 times per day. In other parenteral administration and oral administration, the antibody can be administered in a dose corresponding to the above dose. When the condition is especially severe, the dose may be increased according to the condition.

The antibody of the present invention can be administered directly as it is or as an appropriate pharmaceutical composition. The pharmaceutical composition used for the administration described above comprises the antibody or its salt described above and a pharmacologically acceptable carrier, a diluent or excipient. Such a composition is provided as a dosage form suitable for oral or parenteral administration (e.g., intravenous administration).

Each composition described above may further contain other active components, unless formulation with the antibody described above causes any adverse interaction.

(7) DNA Transgenic Animal

The present invention provides a non-human mammal bearing DNA encoding the protein of the present invention, which is exogenous (hereinafter abbreviated as the exogenous DNA of the present invention) or its variant DNA (sometimes simply referred to as the exogenous variant DNA of the present invention).

That is, the present invention provides:

(1) A non-human mammal bearing the exogenous DNA of the present invention or its variant DNA;

(2) The mammal according to (1), wherein the non-human mammal is a rodent;

(3) The mammal according to (2), wherein the rodent is mouse or rat; and, (4) A recombinant vector containing the exogenous DNA of the present invention or its variant DNA and capable of expressing in a mammal; etc.

The non-human mammal bearing the exogenous DNA of the present invention or its variant DNA (hereinafter simply referred to as the DNA transgenic animal of the present invention) can be prepared by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method, etc. Also, it is possible to transfect the exogenous DNA of the present invention into a somatic cell, a living organ, a tissue cell, or the like by the DNA transfection methods, and utilize the transformant for cell culture, tissue culture, etc. In addition, these cells may be fused with the above-described germinal cell by a publicly known cell fusion method to prepare the DNA transgenic animal of the present invention.

Examples of the non-human mammal that can be used include bovine, swine, sheep, goat, rabbits, dogs, cats, guinea pigs, hamsters, mice, rats, etc. Above all, preferred are rodents, especially mice (e.g., C57Bl/6 strain, DBA2 strain, etc. for a pure line and for a cross line, B6C3F$_1$ strain, BDF$_1$ strain B6D2F$_1$ strain, BALB/c strain, ICR strain, etc.), rats (Wistar, S D, etc.) or the like, since they are relatively short in ontogeny and life cycle from a standpoint of creating model animals for human disease.

"Mammals" in a recombinant vector that can be expressed in the mammals include the aforesaid non-human mammals and human.

The exogenous DNA of the present invention refers to the DNA of the present invention that is once isolated and extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean DNA that expresses the abnormal protein of the present invention and exemplified by the DNA that expresses a protein for suppressing the function of the normal protein of the present invention.

The exogenous DNA of the present invention may be any one of those derived from a mammal of the same species as, or a different species from, the mammal as the target animal. In transfecting the DNA of the present invention, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the protein of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression described above include (1) promoters for DNA derived from viruses (e.g., simian virus, cytomegalovirus, Moloney leukemia virus, JC virus, breast cancer virus, poliovirus, etc.), and (2) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), protein chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among them, cytomegalovirus promoters, human protein elongation factor 1α (EF-1α) promoters, human and fowl β actin promoters, etc., which are capable of high expression in the whole body are preferred.

Preferably, the vectors described above have a sequence that terminates the transcription of the desired messenger RNA in the DNA transgenic animal (generally termed a terminator); for example, a sequence of each DNA derived from viruses and various mammals, and SV40 terminator of the simian virus and the like are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal protein of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of normal protein obtained from the cells or tissues described above by point mutagenesis.

The translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the produced animal will retain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal in which the normal exogenous DNA of the present invention has been transfected can be passaged as the DNA-bearing animal under ordinary rearing environment, after confirming that the exogenous DNA is stably retained by crossing.

By transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

A homozygous animal having the introduced DNA on both of homologous chromosomes can be acquired and male and female of the animal can be bred so that all the progeny retain the DNA in excess.

In a non-human mammal bearing the normal DNA of the present invention, the normal DNA of the present invention has expressed at a high level, and may eventually develop hyperfunction in the function of the protein of the present invention by accelerating the function of endogenous normal DNA. Therefore, the animal can be utilized as a pathologic model animal for such a disease. For example, using the normal DNA transgenic animal of the present invention, it is possible to elucidate the mechanism of hyperfunction in the function of the protein of the present invention and the pathological mechanism of the disease associated with the protein of the present invention and to investigate how to treat these diseases.

Furthermore, since a mammal transfected with the exogenous normal DNA of the present invention exhibits an increasing symptom of the protein of the present invention liberated, the animal is also usable for a screening test of an agent for the prevention and/or treatment of diseases associated with the protein of the present invention, for example, an insulin-sensitizing agent or an agent for the prevention and/or treatment of obesity, hyperlipemia, arteriosclerosis, hypertension or heart disease.

On the other hand, a non-human mammal having the exogenous abnormal DNA of the present invention can be passaged under normal breeding conditions as the DNA-bearing animal after confirming stable retention of the exogenous DNA via crossing. Furthermore, the exogenous DNA of interest can be utilized as a starting material by inserting the DNA into the plasmid described above. The DNA construct with a promoter can be prepared by conventional DNA engineering techniques. The transfection of the abnormal DNA of the present invention at the fertilized egg cell stage is preserved to be present in all of the germinal and somatic cells of the target mammal. The fact that the abnormal DNA of the present invention is present in the germinal cells of the animal after DNA transfection means that all of the offspring of the prepared animal have the abnormal DNA of the present invention in all of the germinal and somatic cells. Such an offspring that inherited the exogenous DNA of the present invention will have the abnormal DNA of the present invention in all of the germinal and somatic cells. A homozygous animal having the introduced DNA on both of homologous chromosomes can be acquired, and by crossing these male and female animals, all the offspring can be bred to retain the DNA.

In a non-human mammal bearing the abnormal DNA of the present invention, the abnormal DNA of the present invention has expressed to a high level, and may eventually develop the function inactive type inadaptability to the protein of the present invention by inhibiting the functions of endogenous normal DNA. Therefore, the animal can be utilized as a pathologic model animal for such a disease. For example, using the transgenic animal expressing the abnormal DNA of the present invention, it is possible to elucidate the mechanism of the function inactive type inadaptability to the protein of the present invention and the pathological mechanism of the disease associated with the protein of the present invention and to investigate how to treat the disease.

Specifically, the transgenic animal of the present invention expressing the abnormal DNA of the present invention at a high level is expected to serve as an experimental model to elucidate the mechanism of the functional inhibition (dominant negative effect) of a normal protein by the abnormal protein of the present invention in the function inactive type inadaptability of the protein of the present invention.

Moreover, a mammal bearing the abnormal exogenous DNA of the present invention has a condition of increasing a free form of the protein of the present invention, and is also available for a screening test of the protein of the present invention or an agent for the improvement or for the prevention and/or treatment of the function inactive type inadaptability, for example, an insulin-sensitizing agent, or an agent for the prevention and/or treatment of obesity, hyperlipemia, arteriosclerosis, hypertension or heart disease.

Other potential applications of two kinds of the DNA transgenic animals of the present invention described above further include:

(1) Use as a cell source for tissue culture;

(2) Elucidation of the relation to a peptide that is specifically expressed or activated by the protein of the present invention, by direct analysis of DNA or RNA in tissues of the DNA transgenic animal of the present invention or by analysis of the peptide tissues expressed by the DNA;

(3) Research on the function of cells derived from tissues that are usually cultured only with difficulty, using cells in tissues bearing the DNA cultured by a standard tissue culture technique;

(4) Screening a drug that enhances the functions of cells using the cells described in (3) above; and, (5) Isolation and purification of the variant protein of the present invention and preparation of an antibody thereto.

Furthermore, clinical conditions of a disease associated with the protein of the present invention, including the function inactive type inadaptability to the protein of the present invention can be determined by using the DNA transgenic animal of the present invention. Also, pathological findings on each organ in a disease model associated with the protein of the present invention can be obtained in more detail, leading to the development of a new method for treatment as well as the research and therapy of any secondary diseases associated with the disease.

Further by withdrawing each organ from the DNA transgenic animal of the present invention, mincing the organ and degrading with a proteinase such as trypsin, etc., it is possible to obtain a free form of the DNA-transfected cell, culture the cells or establish the cell line of cultured cells. Furthermore, the DNA transgenic animal of the present invention can serve to identify cells capable of producing the protein of the present invention, and to study in association with apoptosis, differentiation or propagation or on the mechanism of signal transduction in these properties to inspect any abnormality therein. Thus, the DNA transgenic animal can provide an effective research material for the protein of the present invention and for investigation of its function and effect.

To develop a drug for the treatment of diseases associated with the protein of the present invention, including the function inactive type inadaptability to the protein of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the protein of the present invention, using the DNA transgenic animal of the present invention or a vector capable of expressing the exogenous DNA of the present invention.

(8) Knockout Animal

The present invention provides a non-human mammal embryonic stem cell bearing the DNA of the present invention inactivated and a non-human mammal deficient in expressing the DNA of the present invention.

Thus, the present invention provides:

(1) A non-human mammal embryonic stem cell in which the DNA of the present invention is inactivated;

(2) The embryonic stem cell according to (1), wherein the DNA is inactivated by introducing a reporter gene (e.g., β-galactosidase gene derived from *Escherichia coli*);

(3) The embryonic stem cell according to (1), which is resistant to neomycin;

(4) The embryonic stem cell according to (1), wherein the non-human mammal is a rodent;

(5) The embryonic stem cell according to (4), wherein the rodent is mouse;

(6) A non-human mammal deficient in expressing the DNA of the present invention, wherein the DNA is inactivated;

(7) The non-human mammal according to (6), wherein the DNA is inactivated by inserting a reporter gene (e.g., β-galactosidase derived from *Escherichia coli*) therein and the reporter gene is capable of being expressed under control of a promoter for the DNA of the present invention;

(8) The non-human mammal according to (6), which is a rodent;

(9) The non-human mammal according to (8), wherein the rodent is mouse; and,

(10) A method of screening a compound or its salt that inhibits (preferably inhibits) the promoter activity to the DNA of the present invention, which comprises administering a test compound to the mammal of (7) and detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the protein of the present invention (hereinafter sometimes referred to as the knockout DNA of the present invention) by substantially inactivating the activities of the protein of the present invention encoded by the DNA (hereinafter merely referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained, for example, by isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosi-dase gene) or cat (chloramphenicol acetyltransferase gene), etc. into its exon site thereby to disable the functions of exon, or integrating to a chromosome of the target animal by, e.g., homologous recombination, a DNA sequence that terminates gene transcription (e.g., polyA additional signal, etc.) in the intron between exons, thus inhibiting the synthesis of complete messenger RNA and eventually destroying the gene (hereinafter simply referred to as a targeting vector). The thus-obtained ES cells to the southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may originally be established in accordance with a modification of the known method by Evans and Kaufma described above. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The $BDF_1$ mouse is advantageous in that, when a pathologic model mouse is generated using ES cells obtained therefrom, the genetic background can be changed to that of the C57BL/6 mouse by backcrossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera. It is also desirable that sexes are identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Also, second selection can be achieved by, for example, confirmation of the number of chromosomes by the G-banding method. It is usually desirable that the chromosome number of the obtained ES cells be 100% of the normal number. However, when it is difficult to obtain the cells having the normal number of chromosomes due to physical operations, etc. in the cell establishment, it is desirable that the ES cell is again cloned to a normal cell (e.g., in a mouse cell having the number of chromosomes being 2n=40) after knockout of the gene of the ES cells.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably 5% carbon dioxide and 95% air, or 5% oxygen, 5% carbon dioxide and 90% air) in the presence of LIF (1 to 10000 U/ml) on appropriate feeder cells such as STO fibroblasts, treated with a trypsin/EDTA solution (normally 0.001 to 0.5% trypsin/0.1 to about 5 mM EDTA, preferably about 0.1% trypsin/1 mM EDTA) at the time of passage to obtain separate single cells, which are then plated on freshly prepared feeder cells. This passage is normally conducted every 1 to 3 days; it is desirable that cells be observed at the passage and cells found to be morphologically abnormal in culture, if any, be abandoned.

Where ES cells are allowed to reach a high density in mono-layers or to form cell aggregates in suspension under appropriate conditions, it is possible to differentiate the ES cells to various cell types, for example, parienatal and visceral muscles, cardiac muscle or the like [Nature, 292, 154, 1981; Proc. Natl. Acad. Sci. U.S.A., 78, 7634, 1981; Journal of Embryology Experimental Morphology, 87, 27, 1985]. The cells deficient in expression of the DNA of the present invention, which are obtained from the differentiated ES cells of the present invention, are useful for studying the function of the protein of the present invention cytologically.

The non-human mammal deficient in expression of the DNA of the present invention can be identified from a normal animal by measuring the mRNA level in the subject animal by a publicly known method, and indirectly comparing the degrees of expression.

As the non-human mammal, the same examples supra apply.

With respect to the non-human mammal deficient in expression of the DNA of the present invention, the DNA of the present invention can be made knockout by transfecting a targeting vector, prepared as described above, to mouse embryonic stem cells or mouse oocytes, and conducting homologous recombination in which a targeting vector DNA sequence, wherein the DNA of the present invention is inactivated by the transfection, is replaced with the DNA of the present invention on a chromosome of a mouse embryonic stem cell or mouse embryo.

The knockout cells with the disrupted DNA of the present invention can be identified by the southern hybridization analysis using as a probe a DNA fragment at the site proximal to the DNA of the present invention, or by the PCR analysis using as primers a DNA sequence on the targeting vector and another DNA sequence at the proximal region of other than the DNA of the present invention derived from mouse used in the targeting vector. When non-human mammal stem cells are used, a cell line wherein the DNA of the present invention is inactivated by homologous recombination is cloned; the resulting clones are injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal constructed with both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the protein of the present invention. The individuals deficient in homozygous expression of the protein of the present invention can be obtained from offspring of the intercross between those deficient in heterozygous expression of the protein of the present invention.

When an oocyte is used, a DNA solution may be injected, e.g., into the prenucleus by microinjection thereby to obtain a transgenic non-human mammal having a targeting vector introduced in its chromosome. From such transgenic non-human mammals, those having a mutation at the locus of the DNA of the present invention can be obtained by selection based on homologous recombination.

As described above, the individuals in which the DNA of the present invention is rendered knockout permit passage rearing under ordinary rearing conditions, after the individuals obtained by their crossing have proven to have been knockout.

Furthermore, the genital system may be obtained and retained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell, in which the DNA of the present invention is inactivated, is very useful for preparing a non-human mammal deficient in expression of the DNA of the present invention.

Since the non-human mammal, in which the DNA of the present invention is inactivated, lacks various biological activities derived from the protein of the present invention, such an animal can be a disease model suspected of inactivated biological activities of the protein of the present invention and thus, offers an effective study to investigate the causes for and therapy for these diseases.

(8a) Method of Screening a Compound Having a Therapeutic and/or Preventive Effect on Diseases Caused by Deficiency, Damages, Etc. of the DNA of the Present Invention The non-human mammal deficient in expression of the DNA of the present invention can be employed for screening of a compound having a therapeutic and/or preventive effect on diseases caused by deficiency, damages, etc. of the DNA of the present invention.

That is, the present invention provides a method of screening a compound having a therapeutic and/or preventive effect on diseases caused by deficiency, damages, etc. of the DNA of the present invention, for example, an effect of sensitizing insulin, or a therapeutic and/or preventive effect on obesity, hyperlipemia, arteriosclerosis, hypertension or heart disease, which comprises administering a test compound to a non-human mammal deficient in expression of the DNA of the present invention and, observing and measuring a change occurred in the animal.

As the non-human mammal deficient in expression of the DNA of the present invention, which can be employed for the screening method, the same examples as given hereinabove apply.

Examples of the test compound include peptides, proteins, non-peptide compounds, synthetic compounds, fermentation products, cell extracts, plant extracts, animal tissue extracts, blood plasma, etc. These compounds may be novel compounds or publicly known compounds.

Specifically, the non-human mammal deficient in expression of the DNA of the present invention is treated with a test compound, comparison is made with an intact animal for control and a change in each organ, tissue, disease conditions, etc. of the animal is used as an indicator to assess the therapeutic and/or preventive effects of the test compound.

For treating an animal to be tested with a test compound, for example, oral administration, intravenous injection, etc. are applied, and the treatment can be appropriately selected depending on conditions of the test animal, properties of the test compound, etc. Furthermore, a dose of the test compound to be administered can be appropriately selected depending on the administration route, nature of the test compound, etc.

For screening of the compound having an effect of sensitizing insulin, or a preventive and/or therapeutic effect on, e.g., obesity, hyperlipemia, arteriosclerosis, hypertension or heart disease, a test compound is given to a non-human mammal enhanced in expression of the DNA of the present invention, which suffers from the pathological conditions described above, during fasting, after feeding, or before and after insulin administration. Then, the level of insulin, glucose or free fatty acid contained in blood is observed with passage of time, as compared to the group added with no test compound.

When a test compound is given to a test animal in the screening method above and the aforesaid disease conditions of the test animal are improved at least by about 10%, preferably at least by about 30%, more preferably at least by about 50%, the test compound can be selected as a compound having the therapeutic and/or preventive effects on the diseases described above.

The compound obtained using the above screening method is a compound selected from the test compounds described above and exhibits a preventive and/or therapeutic effect on the diseases caused by deficiencies, damages, etc. of the protein of the present invention. Therefore, the compound can be employed as a safe and low toxic drug such as an agent for the prevention and/or treatment of these diseases. Furthermore, compounds derived from the compound obtained by the screening described above may also be used as well.

The compound obtained by the screening method above may form salts, and may be used in the form of salts with physiologically acceptable acids (e.g., inorganic acids, organic acids, etc.) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

A pharmaceutical which comprises the compound obtained by the above screening method or salts thereof can be manufactured in a manner similar to the method for preparing the pharmaceutical which comprises the protein of the present invention described hereinabove.

As the pharmaceutical preparation thus obtained is safe and low toxic, it can be administered to human or mammal (e.g., rat, mouse, guinea pig, rabbit, sheep, swine, bovine, horse, cat, dog, monkey, etc.).

The dose of the compound or its salt may vary depending upon target disease, subject to be administered, route of administration, etc. For example, when the compound is orally administered, the compound is generally administered to an adult patient (as 60 kg body weight) with insulin resistance in a daily dose of about 0.1 to about 100 mg, preferably about 1.0 to about 50 mg and more preferably about 1.0 to about 20 mg. In parenteral administration, a single dose of the compound may vary depending upon subject to be administered, target disease, etc. When the compound is administered to an adult (as 60 kg body weight) in the form of an injectable preparation, it is advantageous to administer the compound intravenously to the patient with insulin resistance in a daily dose of about 0.01 to about 30 mg, preferably about 0.1 to about 20 mg, and more preferably about 0.1 to about 10 mg. For other animal species, the corresponding dose as converted per 60 kg weight can be administered.

(8b) Method of Screening a Compound that Inhibits the Activity of a Promoter to the DNA of the Present Invention The present invention provides a method of screening a compound or its salts that inhibit the activity of a promoter to the DNA of the present invention, which comprises administering a test compound to a non-human mammal deficient in expression of the DNA of the present invention and detecting the expression of the reporter gene.

In the screening method described above, an animal in which the DNA of the present invention is inactivated by introducing a reporter gene and the reporter gene is expressed under control of a promoter to the DNA of the present invention is used as the non-human mammal deficient in expression of the DNA of the present invention, which is selected from the aforesaid non-human mammals deficient in expression of the DNA of the present invention.

The same examples of the test compound apply to specific compounds used for the screening.

As the reporter gene, the same specific examples apply to this screening method. Preferably, there are used β-galactosidase (lacZ), soluble alkaline phosphatase gene, luciferase gene and the like.

Since the reporter gene is present under control of a promoter to the DNA of the present invention in the non-human mammal deficient in expression of the DNA of the present invention wherein the DNA of the present invention is replaced by the reporter gene, the activity of the promoter can be detected by tracing the expression of a substance encoded by the reporter gene.

When a part of the DNA region encoding the protein of the present invention is substituted with, e.g., β-galactosidase gene (lacZ) derived from *Escherichia coli*, β-galactosidase is expressed in a tissue where the protein of the present invention should originally be expressed, instead of the protein of the present invention. Thus, the state of expression of the protein of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the protein of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or its salt obtained using the screening method described above is the compound that is selected from the test compounds described above and that inhibits the promoter activity to the DNA of the present invention.

The compound obtained by the screening method above may form salts, and may be used in the form of salts with physiologically acceptable acids (e.g., inorganic acids, etc.) or bases (e.g., organic acids, etc.) or the like, especially in the form of physiologically acceptable acid addition salts.

Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compound or its salt that inhibits the promoter activity to the DNA of the present invention can regulate the expression of the protein of the present invention and regulate the function of the protein. Thus, the compound or its salt is useful as an insulin-sensitizing agent, or an agent for the prevention and/or treatment of obesity, hyperlipemia, arteriosclerosis, hypertension or heart disease.

In addition, compounds derived from the compound obtained by the screening described above may also be used as well.

A pharmaceutical which comprises the compound obtained by the above screening method or its salt can be manufactured in a manner similar to the method for preparing the pharmaceutical which comprises the protein of the present invention described hereinabove.

As the pharmaceutical preparation thus obtained is safe and low toxic, it can be administered to human or mammal (e.g., rat, mouse, guinea pig, rabbit, sheep, swine, bovine, horse, cat, dog, monkey, etc.).

A dose of the compound or its salt may vary depending on target disease, subject to be administered, route for administration, etc.; when the compound that inhibits the promoter activity to the DNA of the present invention is orally administered to an adult (as 60 kg body weight), the compound is administered to the patient with insulin resistance normally in a daily dose of about 0.1 to about 100 mg, preferably about 1.0 to about 50 mg and more preferably about 1.0 to about 20 mg. In parenteral administration, a single dose of the compound varies depending on subject to be administered, target disease, etc. but when the compound of inhibiting the promoter activity to the DNA of the present invention is administered to an adult (as 60 kg body weight) in the form of injectable preparation, it is advantageous to administer the compound intravenously to the patient with insulin resistance in a daily dose of about 0.01 to about 30 mg, preferably about 0.1 to about 20 mg and more preferably about 0.1 to about 10 mg. For other animal species, the corresponding dose as converted per 60 kg weight can be administered.

As stated above, the non-human mammal deficient in expression of the DNA of the present invention is extremely useful for screening the compound or its salt that inhibits the promoter activity to the DNA of the present invention and, can greatly contribute to elucidation of causes for various diseases suspected of deficiency in expression of the DNA of the present invention and for the development of preventive and/or therapeutic agent for these diseases.

Also, a so-called transgenic animal (gene transferred animal) can be prepared by using a DNA containing the promoter region of the protein of the present invention, ligating genes encoding various proteins at the downstream and injecting the same into oocyte of an animal. It is thus possible to synthesize the protein therein specifically and study its activity in vivo. When an appropriate reporter gene is ligated to the promoter site described above and a cell line that expresses the gene is established, the resulting system can be utilized as the search system for a low molecular compound having the action of specifically inhibiting the in vivo productivity of the protein of the present invention itself.

(9) Determination of a Ligand to the Protein of the Present Invention

The protein of the present invention, its partial peptide, or a salt thereof is useful as a reagent for searching or determining a ligand to the protein of the present invention or its salt.

The ligand to the protein of the present invention is determined by contacting the protein of the present invention or its salt or the partial peptide of the protein of the present invention or its salt with a test compound.

Examples of the test compound used include tissue extracts from mammal (e.g., human, mouse, rat, swine, bovine, sheep, monkey, etc.), cell culture supernatant, proteins or partial peptides expressed as recombinants by random peptide library or mammal cDNA library, and the like. For example, the tissue extract, cell culture supernatant or the like is added to the protein of the present invention and the mixture is fractionated while assaying the cell stimulating activity so that a single ligand can eventually be obtained. Also, the ligand can be obtained by identifying a binding protein using the binding activity of a random peptide or cDNA library-expressing bacterium or bacteriophage to the protein of the present invention as an indicator, or identifying a binding protein by the yeast two-hybrid technique using a random peptide or cDNA library and yeast expressing the protein, and assaying the cell stimulating activity, etc. from these binding proteins.

Specifically, the method of determining a ligand in the present invention is a method of determining a compound (e.g., a peptide, protein, non-peptide compound, synthetic compound, fermentation product, etc.) or its salt, which binds to the protein of the present invention to induce the cell stimulating activity (the activity of promoting or suppressing, e.g., phosphorylation of the protein of the present invention, phosphorylation of ERK, production of TNF-α, intracellular $Ca^{2+}$ release, change in cell membrane potential, intracellular protein phosphorylation, pH reduction, etc.), by using the protein of the present invention, its partial peptide, or a salt thereof, or by constructing the expression system of recombinant protein and using the receptor binding assay system using the expression system.

The method of determining the ligand in the present invention comprises assaying the amount of a test compound bound to the protein of the present invention or its partial peptide or the cell stimulating activity, when the protein or its partial peptide is brought in contact with the test compound.

More specifically, the present invention provides:

(1) a method of determining a ligand to the protein of the present invention or its salt, which comprises purifying a test compound bound to the protein of the present invention or its salt or the partial peptide of the present invention or its salt, when the tissue extract from a mammal (e.g., human, mouse, rat, swine, bovine, sheep, monkey, etc.), serum, cell culture supernatant, etc. is brought in contact with the protein or its salt or the partial peptide or its salt;

(2) a method of determining a ligand to the protein of the present invention or its salt, which comprises purifying a test compound bound to the protein of the present invention or its partial peptide, when the tissue extract from a mammal (e.g., human, mouse, rat, swine, bovine, sheep, monkey, etc.), serum, cell culture supernatant, etc. is brought in contact with a cell containing the protein or a membrane fraction of the cell;

(3) a method of determining a ligand to the protein of the present invention, which comprises purifying a test compound bound to the protein of the present invention or its partial peptide, when the tissue extract from a mammal (e.g., human, mouse, rat, swine, bovine, sheep, monkey, etc.), serum, cell culture supernatant, etc. is brought in contact with a protein expressed on a cell membrane by culturing a transformant containing a DNA encoding the protein of the present invention;

(4) a method of determining a ligand to the protein of the present invention, which comprises contacting a bacterium or bacteriophage expressing a random peptide or cDNA library on the surface with the protein of the present invention and identifying the amino acid sequence of a peptide binding to the protein;

(5) a method of determining a ligand to the protein of the present invention, which comprises identifying the amino acid sequence of a peptide binding to the protein by the yeast two-hybrid technique using a random peptide or cDNA library and yeast expressing the protein of the present invention;

(6) a method of determining a ligand to the protein of the present invention or its salt, which comprises assaying the protein-mediated cell stimulating activity (the activity of promoting or suppressing, e.g., phosphorylation of the protein of the present invention, phosphorylation of ERK, production of TNF-α, intracellular $Ca^{2+}$ release, change in cell membrane potential, intracellular protein phosphorylation, pH reduction, etc.) in the case where a test compound wherein a binding activity has been found is brought in contact with a cell containing the protein of the present invention; and, (7) a method of determining a ligand to the protein of the present invention or its salt, which comprises assaying the protein-mediated cell stimulating activity (the activity of promoting or suppressing, e.g., phosphorylation of the protein of the present invention, phosphorylation of ERK, production of TNF-α, intracellular $Ca^{2+}$ release, change in cell membrane potential, intracellular protein phosphorylation, pH reduction, etc.) in the case where a protein expressed on a cell membrane by culturing a transformant containing a DNA encoding the protein of the present invention.

a test compound wherein a binding activity has been found is brought in contact with a cell containing the protein of the present invention It is particularly preferred to perform the tests (1) to (5) described above, thereby to confirm that the test compound can bind to the protein of the present invention, followed by the tests (6) and (7) described above.

Any protein is usable as the protein for the ligand determination, so long as it contains the protein of the present invention or the partial peptide of the present invention. However, the protein abundantly expressed using animal cells is appropriate.

To manufacture the protein of the present invention, the expression methods described above are used and preferably, the protein is manufactured by expressing a DNA encoding the protein in mammalian or insect cells. For the DNA fragment encoding the objective protein region, normally the complementary DNA, but not necessarily limited thereto, is employed. For example, the gene fragments or synthetic DNA may also be used. To introduce a DNA fragment encoding the protein of the present invention into host animal cells and efficiently express the DNA there, it is preferred to insert the DNA fragment downstream of a polyhedorin promoter of nuclear polyhedrosis virus (NPV) belonging to baculovirus hosted by insects, SV40-derived promoter, retrovirus promoter, metallothionein promoter, human heat shock promoter, cytomegalovirus promoter, SRα promoter, etc. The quantity and quality of the expressed receptor are examined by publicly known methods, for example, the method described in the literature (J. Biol. Chem., 267, 19555-19559, 1992).

Therefore, in the ligand determination methods of the present invention, the material containing the protein of the present invention, its partial peptide, or a salt thereof, may be a protein purified by publicly known methods, its partial peptide, or a salt thereof, or a cell containing the protein, or a membrane fraction of the cell.

In the ligand determination methods of the present invention, when cells containing the protein of the present invention are used, the cells may be fixed with glutaraldehyde, formalin, etc. The cells can be fixed by publicly known methods.

Cells containing the protein of the present invention refer to host cells that have expressed the protein of the present invention, which host cells include *Escherichia coli*, *Bacillus subtilis*, yeast, insect cells, animal cells, etc.

The cell membrane fraction is a fraction abundant in cell membrane obtained by cell disruption and subsequent fractionation by a publicly known method. Useful cell disruption methods include cell squashing using a Potter-Elvehjem homogenizer, disruption using a Waring blender or Polytron (manufactured by Kinematica, Inc.), disruption by ultrasonication, disruption by cell spraying via a thin nozzle under increased pressure using a French press, and the like. Cell membrane fractionation is effected mainly by fractionation using a centrifugal force, such as centrifugation for fractionation, density gradient centrifugation, etc. For example, cell disruption fluid is centrifuged at a low rate (500 rpm to 3,000 rpm) for a short period of time (normally about 1 to 10 minutes), the resulting supernatant is then centrifuged at a higher rate (15,000 to 30,000 rpm) normally for 30 minutes to 2 hours. The precipitate thus obtained is used as the membrane fraction. The membrane fraction is abundant in the protein expressed and membrane components such as cell-derived phospholipids, membrane proteins, etc.

The amount of the protein in the cells containing the protein and in the membrane fraction is preferably $10^3$ to $10^8$ molecules per cell, more preferably $10^5$ to $10^7$ molecules per cell. As the level of expression is enhanced, the ligand binding activity per unit of the membrane fraction (specific activity) increases so that not only a highly sensitive screening system can be constructed but also large quantities of samples can be assayed with the same lot.

The ligand to the protein of the present invention or its salt is determined by the following procedures. First, a preparation of the protein of the present invention is prepared by suspending a cell containing the protein of the present invention or a membrane fraction of the cell in a buffer appropriate for use in the determination method. Any buffer may be used if it does not interfere with the ligand-protein binding, such buffers including a phosphate buffer, a Tris-HCl buffer, etc., having a pH of 4 to 10 (preferably a pH of 6 to 8). For the purpose of minimizing non-specific binding, a surfactant such as CHAPS, Tween-80™ (Kao-Atlas Inc.), digitonin, deoxycholate, etc., or various proteins such as bovine serum albumin, gelatin or the like, may optionally be added to the buffer. Further for the purpose of suppressing the degradation of the receptor or ligand by protease, a protease inhibitor such as PMSF, leupeptin, E-64 (manufactured by Peptide Institute, Inc.), pepstatin, etc. may also be added. A given amount (5,000 cpm to 500,000 cpm) of the test compound labeled with $[^3H]$, $[^{125}I]$, $[^{14}C]$, $[^{35}S]$ or the like is added to 0.01 ml to 10 ml of the receptor solution. To determine the amount of non-specific binding (NSB), a reaction tube containing an unlabeled test compound in a large excess is prepared as well.

The reaction is carried out approximately at 0 to 50° C., preferably about 4 to 37° C. for about 20 minutes to about 24 hours, preferably about 30 minutes to about 3 hours. After completion of the reaction, the reaction mixture is filtrated through glass fiber filter paper, etc. and rinsed with an appropriate amount of the same buffer. The residual radioactivity in the glass fiber filter paper is then measured by means of a liquid scintillation counter or a γ-counter. A test compound exceeding 0 cpm in count obtained by subtracting nonspecific binding (NSB) from the total binding (B) (B minus NSB) can be selected as a ligand to the protein of the present invention or its salt.

The method (6) or (7) above for determining a ligand to the protein of the present invention or its salt can be performed as follows. The protein-mediated cell-stimulating activity (the activity of promoting or suppressing, e.g., phosphorylation of the protein of the present invention, phosphorylation of ERK, production of TNF-α, intracellular $Ca^{2+}$ release, change in cell membrane potential, intracellular protein phosphorylation, pH reduction, etc.) can be assayed by a publicly known method, or using an assay kit commercially available. Specifically, cells containing the protein are cultured on a multi-well plate, etc. Prior to the ligand determination, the medium is replaced with fresh medium or with an appropriate non-cytotoxic buffer, followed by incubation for a given period of time in the presence of a test compound, etc. Subsequently, the cells are extracted or the supernatant is recovered and the product formed is quantified by appropriate procedures. Where it is difficult to detect the production of an indicator substance for the cell stimulating activity due to a degrading enzyme contained in the cells, an inhibitor against such a degrading enzyme may be added prior to the assay.

The kit of the present invention for determining a ligand that binds to the protein of the present invention or its salt comprises the protein of the present invention or its salt, the partial peptide of the present invention or its salt, a cell containing the protein of the present invention, or a membrane fraction of the cell containing the protein of the present invention.

Examples of the ligand determination kit of the present invention are given below.

1. Reagent for Ligand Determination (1) Assay Buffer and Wash Buffer

Hanks' Balanced Salt Solution (manufactured by Gibco Co.) supplemented with 0.05% bovine serum albumin (Sigma Co.).

The solution is sterilized by filtration through a 0.45 μm filter and stored at 4° C. Alternatively, the solution may be prepared at use.

(2) Preparation of the Protein of the Present Invention

CHO cells on which the protein of the present invention has been expressed are subcultured in a 12-well plate at the rate of $5 \times 10^5$ cells/well and then cultured at 37° C. under 5% $CO_2$ and 95% air for 2 days.

(3) Labeled Test Compound

A compound labeled with commercially available [$^3$H], [$^{125}$I], [$^{14}$C], [$^{35}$S], etc., or a compound labeled by appropriate methods.

An aqueous solution of the compound is stored at 4° C. or −20° C. The solution is diluted to 1 μM with an assay buffer at use. A sparingly water-soluble test compound is dissolved in dimethylformamide, DMSO, methanol, etc.

(4) Unlabeled Test Compound

Unlabeled form of the same test compound is prepared in a concentration 100 to 1,000-fold higher than that of the labeled compound.

2. Assay Procedures (1) CHO cells capable of expressing the protein of the present invention are cultured in a 12-well culture plate. After washing twice with 1 ml of assay buffer, 490 μl of the assay buffer is added to each well.

(2) After 5 μl of a labeled test compound is added, the resulting mixture is incubated at room temperature for an hour. To determine the non-specific binding, 5 μl of unlabeled compound is added to the system.

(3) The reaction mixture is removed and the wells are washed 3 times with 1 ml of wash buffer. The labeled test compound bound to the cells is dissolved in 0.2N NaOH-1% SDS and then mixed with 4 ml of liquid scintillator A (manufactured by Wako Pure Chemical Industries, Ltd.).

(4) The radioactivity is measured using a liquid scintillation counter (manufactured by Beckman Co.).

In the specification, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
pGlu: pyroglutamic acid
Sec: selenocysteine Substituents, protecting groups and reagents frequently used in this specification are presented as the codes below.

Me: methyl group
Et: ethyl group
Bu: butyl group
Ph: phenyl group
TC: thiazolidine-4(R)-carboxamide group
Tos: p-toluenesulfonyl
CHO: formyl
Bzl: benzyl
$Cl_2$-Bzl: 2,6-dichlorobenzyl
Bom: benzyloxymethyl
Z: benzyloxycarbonyl
Cl-Z: 2-chlorobenzyloxycarbonyl
Br-Z: 2-bromobenzyl oxycarbonyl
Boc: t-butoxycarbonyl
DNP: dinitrophenol
Trt: trityl
Bum: t-butoxymethyl
Fmoc: N-9-fluorenyl methoxycarbonyl
HOBt: 1-hydroxybenztriazole
HOOBt: 3,4-dihydro-3-hydroxy-4-oxo-1,2,3-benzotriazine
HONB: 1-hydroxy-5-norbornene-2,3-dicarboxylmide
DCC: N,N'-dichlorohexylcarbodiimide The sequence identification numbers in the sequence listing of the specification indicate the following sequences.

[SEQ ID NO: 1]
This shows the amino acid sequence of human TREM-2.

[SEQ ID NO: 2]
This shows the amino acid sequence of mouse TREM-2.

[SEQ ID NO: 3]
This shows the base sequence of DNA encoding human TREM-2 having the amino acid sequence represented by SEQ ID NO: 1.

[SEQ ID NO: 4]
This shows the base sequence of DNA encoding mouse TREM-2 having the amino acid sequence represented by SEQ ID NO: 2.

[SEQ ID NO: 5]
This shows the base sequence of the primer used in EXAMPLE 1.

[SEQ ID NO: 6]
This shows the base sequence of the primer used in EXAMPLE 1.

[SEQ ID NO: 7]
This shows the base sequence of the primer used in EXAMPLE 2.

[SEQ ID NO: 8]
This shows the base sequence of the primer used in EXAMPLE 2.

[SEQ ID NO: 9]
This shows the base sequence of the primer used in EXAMPLE 2 and EXAMPLE 3.

[SEQ ID NO: 10]
This shows the base sequence of the primer used in EXAMPLE 2 and EXAMPLE 3.

[SEQ ID NO: 11]
This shows the base sequence of the primer used in EXAMPLE 6.

[SEQ ID NO: 12]
This shows the base sequence of the primer used in EXAMPLE 6.

[SEQ ID NO: 13]
This shows the base sequence of the primer used in EXAMPLE 6.

[SEQ ID NO: 14]
This shows the base sequence of the primer used in EXAMPLE 6.

[SEQ ID NO: 15]
This shows the base sequence of the primer used in EXAMPLE 6.

[SEQ ID NO: 16]
This shows the base sequence of the primer used in EXAMPLE 6.

Hereinafter, the present invention will be described more specifically with reference to EXAMPLES, but is not intended to limit the present invention thereto.

EXAMPLE 1

Search of Expression-Shifted Gene

Epididymis adipose tissues were excised from KKA$^y$ mouse (14 weeks old, male) and C57BL/6 mouse (14 weeks old, male), homogenized in ISOGEN reagent (Wako Pure Chemical Industries, Ltd.) and extracted with chloroform followed by isopropanol precipitation to extract total RNAs from the respective tissues. From the total RNAs, poly (A)$^+$ RNAs were further purified with Oligotex dT30 (Takara Bio Inc.). Using 2 µg of these poly (A)$^+$ RNAs as the starting material, cDNA was synthesized by Reverse Transcriptase (Superscript RTII; Invitrogen). Using PCR-Select cDNA Subtraction Kit (Clontech), the group of cDNA, which expression level increased or decreased in the KKA$^y$ mouse adipose tissue, was selectively amplified as PCR fragment. After ligation of the amplified cDNA group to cloning vector pT7 Blue-T, cloning was effected by transforming *Escherichia coli* DH5α. The respective insertion sequences were amplified by vector sequences M13 primer P7 (SEQ ID NO: 5) and M13 primer P8 (SEQ ID NO: 6) (both Toyobo). The resulting PCR fragments were spotted onto glass slides to prepare microarrays. Poly (A)$^+$ RNA derived from the adipose tissue in each mouse was fluorescence-labeled with Cy5 or Cy3 by random priming to prepare a detection probe, which was hybridized to microarray for 15 hours. The gene groups showing a marked difference in the expression level were identified. When compared to the C57BL/6 mouse expression gene for control, 29 genes were identified as genes with increased expression in KKA$^y$ by 4 times or more; on the other hand, 69 genes were identified as genes with decreased expression by 4 times or less. Mouse TREM-2 was identified to be a gene with increased expression by 5.32 times in the gene group with increased expression.

EXAMPLE 2

Cloning of TREM-2 from Adipocytes

In order to acquire experimental materials for confirmation of expression shift of TREM-2 and for its function analysis, the full-length coding region cDNA of TREM-2 was cloned by PCR from cDNA libraries of human adipocyte and mouse 3T3-L1 adipocyte.

For cloning of human TREM-2, the following sequences were used as primers.

5'-ATGGAGCCTCTCCGGCTGCTCATC-3'    (SEQ ID NO: 7)

5'-TCACGTGTCTCTCAGCCCTGGCAG-3'    (SEQ ID NO: 8)

Using Advantage-2 cDNA PCR Kit (Clontech), the reaction was carried out in 35 cycles with one cycle set at 98° C. for 20 seconds and 68° C. for 1 minute and 30 seconds.

For cloning of mouse TREM-2, the following sequences were used as primers.

5'-ATGGGACCTCTCCACCAGTTTCTCCTG-3'    (SEQ ID NO: 9)

5'-TCACGTACCTCCGGGTCCAGTGAG-3'    (SEQ ID NO: 10)

Using Pfu Turbo DNA polymerase (Stratagene), the reaction was carried out in 35 cycles with one cycle set at 95° C. for 20 seconds, 65° C. for 40 seconds and 72° C. for 1 minute. The cDNA fragment obtained with human TREM-2 was used as it was. On the other hand, the cDNA fragment obtained with mouse TREM-2 was reacted on TAKARA Ex-Taq (Takara Bio Inc.) at 72° C. for 10 minutes to add A at the both 3' ends of the PCR fragment. Thereafter, the cDNA fragments were cloned to pCR2.1 vector (Invitrogen), respectively, followed by DNA sequencing. TREM-2 isolated from human adipocyte coincided with known human TREM-2 (AF213457). On the other hand, 3 cDNAs of TREM-2a (AY024348), TREM-2b (AY024349) and TREM-2c (AF213458) are present as known sequences for mouse TREM-2; in TREM-2 acquired from 3T3-L1 adipocyte, 6 clones obtained were all coincident with TREM-2a.

EXAMPLE 3

Confirmation of Expression Shift by RT-PCR

RNAs extracted from epididymis adipose tissues of KKA$^y$ mouse (14 weeks old, male) and C57BL/6 mouse (14 weeks old, male) were subjected to RT-PCR. Using an Oligo-dT-adapter primer (Takara Bio Inc.), cDNA was synthesized with AMV (Avian Myeloblastosis Virus)-derived reverse transcriptase (Takara Bio Inc.) from 0.5 μg of total RNA extracted from each tissue. PCR was then conducted using primers (SEQ ID NO: 9 and SEQ ID NO: 10) for mouse TREM-2 cloning. Using Advantage-2 cDNA PCR Kit (Clontech), the reaction was carried out in 25 cycles with one cycle set at 98° C. for 20 seconds and 68° C. for 1 minute and 30 seconds. By detecting the reaction product on agarose gel electrophoresis, it could be confirmed that there was a difference in the TREM-2 expression level in KKA$^y$ mouse adipose tissue by 5 times or more than the TREM-2 expression level in C57BL/6 mouse, as in the results with the microarray in EXAMPLE 1.

EXAMPLE 4

Production of Anti-Mouse TREM-2 Antibody and Analysis of TREM-2 Expression in Mouse Adipose Tissue on a Protein Level A rabbit was immunized with a peptide constructed from 133 Leu to 147 Ser in mouse TREM-2 sequence [SEQ ID NO: 2] as an antigen to acquire anti-TREM-2 polyclonal antibody. Using this antibody, 20 μg each of the homogenates from the excised epididymis adipose tissues of KKA$^y$ mouse and C57BL/6 mouse was analyzed by western blotting. The band of TREM-2 was detected from the KKA$^y$ mouse-derived tissue, whereas any band was not detected from the C57BL/6 mouse-derived tissue.

EXAMPLE 5

Distribution of TREM-2-Expressed Tissues in Mice

Total RNAs were extracted from the epididymis adipose tissue, mesenteric adipose tissue, skeletal muscle, liver, testis, spleen, brain and kidney of KKA$^y$ mouse and C57BL/6 mouse, respectively. Distribution of TREM-2-expressed tissues was then analyzed by RT-PCR described in EXAMPLE 3. A marked expression was noted in the epididymis adipose tissue and mesenteric adipose tissue in KKA$^y$ mouse. On the other hand, expression was barely noted in tissues other than these adipose tissues.

EXAMPLE 6

Quantification of TREM-2 in Diabetes Model Mouse (1) Quantitative RT-PCR

The copy number of TREM-2 mRNA per 1 ng of total RNA was determined by quantitative RT-PCR. Using SYBR Green RT-PCR reagent kit RT-PCR (Applied Biosystems), RT-PCR was carried out in accordance with the protocol attached and the PCR product was quantified on the PCR product automated detection and/or quantification system or ABI PRISM 7700 (Applied Biosystems).

For the quantitative RT-PCR of mouse TREM-2, the following primers were used.

5'-ACACCCTTGCTGGAACCGTCAC-3'    (SEQ ID NO: 11)

5'-GTCCTCCAGCACCTCCACCAGTA-3'    (SEQ ID NO: 12)

For the quantitative RT-PCR of human TREM-2, the following primers were used.

5'-GAGTCTGAGAGCTTCGAGGATG-3'    (SEQ ID NO: 13)

5'-CTGGCTGCTAGAATCTTGATGA-3',    (SEQ ID NO: 14)

For the quantitative RT-PCR of mouse TNF-α, the following primers were used.

5'-AAGGGATGAGAAGTTCCCAAA-3'    (SEQ ID NO: 15)

5'-CTCCACTTGGTGGTTTGCTAC-3'    (SEQ ID NO: 16)

(2) Relation of the Progress of Pathological Conditions of Diabetes in Animal Model for Diabetes to the Expression of TREM-2

The expression level of TREM-2 mRNA was quantified by the quantitative RT-PCR described in EXAMPLE 6 (1). In the epididymis adipose tissue and mesenteric adipose tissue in KKA$^y$ mouse, a markedly enhanced expression level by at least 10 times was noted when compared to C57BL/6 mouse. The expression level of TREM-2 mRNA in KKA$^y$ mice of 7, 14 and 28 weeks old was assayed in a similar manner. The expression level increased in proportion to blood glucose enhanced with the age of weeks. In this case, the mRNA expression level of TNF-α as an indicator of insulin resistance increased as in TREM-2. The correlation coefficient ($R^2$ value) in expression level between TREM-2 and TNF-α was 0.8802.

On the other hand, the expression of TREM-2 mRNA was quantified in the epididymis adipose tissue of db/db mice of 11, 20 and 40 weeks old by the same manner as described above. In this case, too, the expression increased in proportion to blood glucose with the age of weeks, as in KKA$^y$ mice.

EXAMPLE 7

Analysis of TREM-2 Expression in 3T3-L1 Adipocyte in the Insulin Resistant State Insulin is chronically acted on 3T3-L1 adipose tissue, whereby the insulin resistant state can be experimentally generated on tissue culture level (Diabetologia, 38, 1148-1156, 1995; J. Biol. Chem., 272, 7759-7764, 1997). The TREM-2 expression level in 3T3-L1 cells, which were rendered resistant to insulin by this procedure, was assayed by the quantitative RT-PCR described in EXAMPLE 6 (1).

When 100 nM of insulin was added to 3T3-L1 adipose tissue for 48 hours, the TREM-2 mRNA expression level increased by at least 3 times. Also, when 2 µM of insulin was added for 48 hours, the TREM-2 mRNA expression level increased by at least 6 times.

EXAMPLE 8

Analysis of TREM-2 Expression in Normal Human Tissues

To analyze expression of TREM-2 mRNA in the brain, colon, heart, kidney, leukocyte, liver, lung, ovary, pancreas, prostate gland, placenta, skeletal muscle, small intestine, spleen, testis and thymus derived from normal human, RT-PCR was carried out with the primers used for the cDNA cloning described in EXAMPLE 2, according to a modification of the procedure described in EXAMPLE 3.

Expression of TREM-2 mRNA could be hardly confirmed in any of the tissues.

EXAMPLE 9

Analysis of TREM-2 Expression in Adipose Tissue of Human Patient with Diabetes

Total RNAs were extracted from the subcutaneous adipose tissues in human patients with diabetes, and the level of TREM-2 mRNA contained therein was compared to the level in non-diabetic patients by the quantitative RT-PCR described in EXAMPLE 6 (1).

Expression of TREM-2 was barely noted in any of 6 non-diabetic patients, whereas in the patients with diabetes, markedly enhanced expression of TREM-2 was noted in 3 out of 8 cases by at least 10 times, when compared to the non-diabetic patients.

EXAMPLE 10

Study on Hypoglycemic Effect of TREM-2 Extracellular Domain in Diabetic Model Animal In order to study the suppressed function of TREM-2 by neutralization of TREM-2 ligand with TREM-2 ligand with TREM-2 extracellular domain (hereinafter briefly referred to as Sol TREM-2), an experiment was conducted to administer the same to KKA$^y$ mouse.

Sol TREM-2 was produced as an *Escherichia coli* recombinant protein having 4 amino acids (Gly-Ser-His-Met) (SEQ ID NO: 17) corresponding to the extracellular domain, which were added to mouse TREM-2 sequence (SEQ ID NO: 2) at the N terminus of a polypeptide consisting of 147 amino acids from the 18th Ala to the 164th Glu in constructing a recombinant protein expression vector. Sol TREM-2 was administered intraperitoneally to KKA$^y$ mice (14 weeks old, male) in 4 times, i.e., 3, 2 and 1 day before glucose tolerance test and on the day of glucose tolerance test, respectively in a dose of 100 µg each, thus in the total dose of 400 µg. After administration of Sol TREM-2, 1 g/kg of glucose was intraperitoneally administered to each mouse to cause glucose tolerance to load glucose, and blood glucose was measured until 2 hours after the glucose loading.

A marked reduction in blood glucose was noted with the Sol TREM-2-administered mice from 30 minutes after the glucose loading, when compared to the control mice. A blood glucose reduction to about 100 mg/dL was observed from 60 minutes to 120 minutes. Also, when the area under glucose curve (AUC) values for blood glucose from immediately after the glucose loading to 120 minutes were compared in this experiment, a significant reduction in AUC values by about 70% was noted in the Sol TREM-2-administered mice as compared to the control mice.

The mRNA expression level of TNF-α in the epididymis white adipose tissue after Sol TREM2 administration was measured by the quantitative RT-PCR described in EXAMPLE 6 (1), which results showed a reduction to 50% or less.

The frequency of dosing was increased to 8 times during the period of from 7 days before the glucose tolerance test to the day of the glucose tolerance test, whereby the hypoglycemic effect became more remarkable. The fasting blood glucose in the group administered with no Sol TREM-2 showed about 250 mg/dL, whereas the fasting blood glucose in the Sol TREM-2-administered group was reduced to almost normal level of about 140 mg/dL.

In this case, the blood insulin level in the Sol TREM-2-administered group was reduced to 73% of the group administered with no Sol TREM-2.

EXAMPLE 11

Study of Hypolipemic Effect by TREM-2 Extracellular Domain on Diabetic Model Animal Sol TREM2 was administered to KKA$^y$ mice in 8 times by the procedure described in EXAMPLE 10. Then blood was collected and blood fat was determined.

In KKA$^y$ mice of the Sol TREM-2-administered group, blood triglycerides and non-esterified fatty acid were reduced to 63% and 68%, respectively, when compared to the group administered with no Sol TREM-2.

EXAMPLE 12

Screening 1 of Insulin Resistance Improving Compounds Using the TREM-2 Inhibitory Activity as an Indicator Human or mouse TREM-2 gene is introduced into 3T3-L1 cells or COS7 cells to acquire the cell line stably expressing TREM-2. A compound for activating TREM2, an antibody, a naturally occurring TREM-2 ligand, KKA$^y$ mouse adipose tissue homogenate or serum is brought in contact with the cells to activate TREM-2. The activation of TREM-2 is confirmed by publicly known techniques, for example, by monitoring phosphorylation of TREM-2, phosphorylation of DAP12 as a protein intracellularly interactive with TREM-2, phosphorylation of intracellular signal transduction molecules (ERK, etc.), expression of TNF-α, or the like.

A test compound is added to the TREM-2-activated cells. The same techniques as those for confirming the activation of TREM-2 described above are used to screen compounds inactivating TREM-2 signal.

The screened compounds are confirmed by MTT assay to be non-cytotoxic, and then undergo secondary assessment to select compounds having improved insulin resistance.

In the secondary assessment, on a tissue culture level, enhanced insulin receptor or IRS protein tyrosine phosphorylation, suppressed IRS protein serine phosphorylation or the like is employed as an indicator to select insulin resistance improving compounds.

The selected compounds are further given to KKA$^y$ mice followed by screening in terms of glucose tolerance test, insulin resistance test or expression of TNF-α as the indicator. The compounds having the insulin-sensitizing activity in vivo are thus selected.

EXAMPLE 13

Screening 2 of Insulin-Sensitizing Compounds Using the TREM-2 Inhibitory Activity as an Indicator Mice are immunized with human TREM-2 extracellular domain (polypeptide containing the 14th Glu to the 170th Pro in the amino acid sequence represented by SEQ ID NO: 1) as an antigen to produce a plurality of anti-TREM-2 monoclonal antibodies.

Human or mouse TREM-2 gene is introduced into 3T3-L1 cells or COS7 cells to acquire the cell line stably expressing TREM-2. The anti-TREM-2 monoclonal antibodies described above are acted on the cells and the antibodies to activate TREM-2 are selected. The activation of TREM-2 is confirmed by publicly known techniques, for example, by monitoring phosphorylation of TREM-2, phosphorylation of DAP12 as a protein intracellularly interactive with TREM-2, phosphorylation of intracellular signal transduction molecules (ERK, etc.), expression of TNF-α, or the like.

A test compound is added to the TREM-2-activated cells. The same techniques as those for confirming the activation of TREM-2 described above are used to screen compounds inactivating TREM-2 signal.

The screened compounds are confirmed as described in EXAMPLE 12 to be non-cytotoxic and to have the insulin-sensitizing activity on a culture cell level and on an animal level.

EXAMPLE 14

Screening of Insulin-Sensitizing Compounds Using TREM-2 Expression Inhibition as an Indicator After cDNA of a green fluorescent protein or β-galactosidase is ligated with human TREM-2 promoter sequence as a reporter gene, which is then introduced into 3T3-L1 or CHO cells.

Using the same techniques as described in EXAMPLE 11, the TREM-2 promoter activity is enhanced and a test compound is added to the cells. The compounds inhibiting TREM-2 promoter activity are thus screened.

The screened compounds are confirmed as described in EXAMPLE 12 to be non-cytotoxic and to have the insulin-sensitizing activity on a culture cell level and on an animal level.

INDUSTRIAL APPLICABILITY

The protein of the present invention provides enhanced expression in adipose tissues and has an effect of inducing or aggravating insulin resistance to increase blood glucose and blood fat levels.

Therefore, pharmaceuticals which comprises the antisense polynucleotide of the present invention, the compound or its salt that inhibits the expression of the protein gene of the present invention or the antibody of the present invention can be used, for example, as insulin-sensitizing agents, or further as agents for the prevention and/or treatment of diabetes, obesity, hyperlipemia, arteriosclerosis, hypertension or heart disease.

Therefore, the protein of the present invention is a marker for diagnosis of insulin resistance, obesity, hyperlipemia, arteriosclerosis, hypertension or heart disease.

Furthermore, the compound or its salt that inhibits the activity of the protein, the compound or its salt that inhibits the expression of a gene for the protein, the extracellular domain of the protein, the neutralizing antibody that inhibits the activity of the protein, and the antisense polynucleotide of the present invention have, for example, the insulin-sensitizing activity to diminish blood glucose and blood fat levels. Thus, they can be used as pharmaceuticals including, e.g., insulin-sensitizing agents, agents for the prevention and/or treatment of obesity, hyperlipemia, arteriosclerosis, hypertension or heart disease, and so on.

The protein of the present invention and the polynucleotide encoding the protein are useful for screening excellent insulin-sensitizing agents, agents for the prevention and/or treatment of obesity, hyperlipemia, arteriosclerosis, hypertension or heart disease, and so on.

The invention claimed is:

1. A method of screening an insulin-sensitizing agent, which comprises:
   (i) preparing a cell line which expresses a protein comprising the amino acid sequence of SEQ ID NO: 1 or SEQ ID NO: 2, or a salt thereof;
   (ii) adding KKA$^y$ mouse adipose tissue homogenate or serum to the cell line so as to activate the protein;
   (iii) adding a test compound to the activated cell line and determining whether or not the test compound inactivates the protein; and
   (iv) selecting a test compound that inactivates the protein;
   wherein said inactivation of the protein is verified by monitoring phosphorylation of the protein, phosphorylation of DNAX-activation protein 12 (DAP12) intracellularly interacting with the protein, phosphorylation of extracellular signal-regulated kinase (ERK), or expression of TNF-α,
   wherein decreased phosphorylation or TNF-α expression is indicative of an insulin-sensitizing agent.

2. A method of screening an insulin-sensitizing agent, which comprises:
   (i) preparing a cell line which expresses a protein comprising the amino acid sequence of SEQ ID NO: 2, or a salt thereof;
   (ii) adding an antibody against the protein, KKA$^y$ mouse adipose tissue homogenate or serum to the cell line so as to activate the protein;
   (iii) adding a test compound to the activated cell line and determining whether or not the test compound inactivates the protein; and
   (iv) selecting a test compound that inactivates the protein;
   wherein said inactivation of the protein is verified by monitoring phosphorylation of the protein, phosphorylation of DAP12 intracellularly interacting with the protein, phosphorylation of ERK, or expression of TNF-α,
   wherein decreased phosphorylation or TNF-α expression is indicative of an insulin-sensitizing agent.

3. A method of screening an insulin-sensitizing agent, which comprises:
   (i) preparing a cell line which expresses a protein comprising the amino acid sequence consisting of 147 amino acids from the 18$^{th}$ Ala to the 164$^{th}$ Glu of the amino acid sequence of SEQ ID NO: 2, or a salt thereof;
   (ii) adding an antibody against the protein, KKA$^y$ mouse adipose tissue homogenate or serum to the cell line so as to activate the protein;
   (iii) adding a test compound to the activated cell line and determining whether or not the test compound inactivates the protein; and
   (iv) selecting a test compound that inactivates the protein;
   wherein said inactivation of the protein is verified by monitoring phosphorylation of the protein, phosphorylation of DAP12 intracellularly interacting with the protein, phosphorylation of ERK, or expression of TNF-α,
   wherein decreased phosphorylation or TNF-α expression is indicative of an insulin-sensitizing agent.

4. A kit for screening an insulin-sensitizing agent by the method of claim 1, wherein said kit comprises a cell producing a protein comprising the amino acid sequence of SEQ ID NO: 2, or a salt thereof.

5. A method of screening an agent for the treatment of diabetes, which comprises:
   (i) preparing a cell line which expresses a protein comprising the amino acid sequence of SEQ ID NO: 1 or SEQ ID NO: 2, or a salt thereof;
   (ii) adding KKA$^y$ mouse adipose tissue homogenate or serum to the cell line so as to activate the protein;
   (iii) adding a test compound to the activated cell line and determining whether or not the test compound inactivates the protein; and
   (iv) selecting a test compound that inactivates the protein;
   wherein said inactivation of the protein is verified by monitoring phosphyorlation of the protein, phosphorylation of DAP12 intracellularly interacting with the protein, phosphorylation of ERK, or expression of TNF-α,
   wherein decreased phosphorylation or TNF-α expression is indicative of an agent for the treatment of diabetes.

6. A kit for screening an agent for the treatment of diabetes by the method of claim 5, wherein said kit comprises
   (i) a cell producing a protein comprising the amino acid sequence of SEQ ID NO: 2, or a salt thereof.

7. The screening method according to claim 1, further comprising assessing insulin-sensitizing activity of the selected compound, wherein said assessing of insulin-sensitizing activity is performed on a tissue culture level based on enhanced insulin receptor substrate (IRS) protein tyrosine phosphorylation or suppressed IRS protein serine phosphorylation, or on an animal level using a glucose tolerance test, insulin sensitization test or expression of TNF-α as the indicator.

8. A kit for screening an insulin-sensitizing agent by the method of claim 1, wherein said kit comprises:
   (i) a cell producing a protein comprising the amino acid sequence of SEQ ID NO: 2, or a salt thereof; and
   (ii) (a) an agent for detecting insulin receptor or IRS protein, and an agent for detecting phosphorylated tyrosine or phosphorylated serine; (b) an agent for detecting tyrosine-phosphorylated IRS protein or insulin receptor; (c) an agent for detecting serine-phosphorylated IRS protein; or (d) KKA$^y$ mouse.

9. A kit for screening an insulin-sensitizing agent, wherein said kit comprises:
   (i) a protein comprising the amino acid sequence of SEQ ID NO: 2, or a salt thereof; and
   (ii) (a) an agent for detecting insulin receptor or IRS protein, and an agent for detecting phosphorylated tyrosine or phosphorylated serine; (b) an agent for detecting tyrosine-phosphorylated IRS protein or insulin receptor; (c) an agent for detecting serine-phosphorylated IRS protein; or (d) KKA$^y$ mouse.

10. A kit for screening an agent for the treatment of diabetes by the method of claim 5, wherein said kit comprises
    (i) a cell capable of producing a protein comprising the amino acid sequence of SEQ ID NO: 2, or a salt thereof; and
    (ii) (a) an agent for detecting insulin receptor or IRS protein, and an agent for detecting phosphorylated tyrosine or phosphorylated serine; (b) an agent for detecting tyrosine-phosphorylated IRS protein or insulin receptor; (c) an agent for detecting serine-phosphorylated IRS protein; or (d) KKA$^y$ mouse.

11. A kit for screening an agent for the treatment of diabetes, wherein said kit comprises
    (i) a protein comprising the amino acid sequence of SEQ ID NO: 2, or a salt thereof; and
    (ii) (a) an agent for detecting insulin receptor or IRS protein, and an agent for detecting phosphorylated tyrosine or phosphorylated serine; (b) an agent for detecting tyrosine-phosphorylated IRS protein or insulin receptor; (c) an agent for detecting serine-phosphorylated IRS protein; or (d) KKA$^y$ mouse.

12. A method of screening an insulin-sensitizing agent, which comprises:
    (i) preparing a cell line which expresses a protein comprising the amino acid sequence of SEQ ID NO: 1 or SEQ ID NO: 2, or a salt thereof;
    (ii) adding an antibody against the protein, KKA$^y$ mouse adipose tissue homogenate or serum to the cell line so as to activate the protein;
    (iii) adding a test compound to the activated cell line and determining whether or not the test compound inactivates the protein; and
    (iv) selecting a test compound that inactivates the protein;
    wherein said inactivation of the protein is verified by monitoring phosphorylation of the protein, phosphorylation of DAP12 intracellularly interacting with the protein, phosphorylation of ERK, or expression of TNF-α,
    wherein decreased phosphorylation or TNF-α expression is indicative of an insulin-sensitizing agent,
    and wherein said method further comprises: (v) assessing insulin-sensitizing activity of the selected compound, wherein said assessing of insulin-sensitizing activity is performed on a tissue culture level based on enhanced IRS protein tyrosine phosphorylation or suppressed IRS protein serine phosphorylation, or on an animal level using glucose tolerance test, insulin sensitization test or expression of TNF-α as the indicator.

13. A kit for screening an insulin-sensitizing agent by a method of screening an insulin-sensitizing agent, wherein said method comprises:
    (i) preparing a cell line which expresses a protein comprising the amino acid sequence of SEQ ID NO: 1 or SEQ ID NO: 2, or a salt thereof;
    (ii) adding an antibody against the protein, KKA$^y$ mouse adipose tissue homogenate or serum to the cell line so as to activate the protein;
    (iii) adding a test compound to the activated cell line and determining whether or not the test compound inactivates the protein; and
    (iv) selecting a test compound that inactivates the protein;
    wherein said inactivation of the protein is verified by monitoring phosphorylation of the protein, phosphorylation of DAP12 intracellularly interacting with the protein, phosphorylation of ERK, or expression of TNF-α,
    wherein decreased phosphorylation or TNF-α expression is indicative of an insulin-sensitizing agent, and
    wherein said kit comprises:
    (i) a cell producing a protein comprising the amino acid sequence of SEQ ID NO: 1 or SEQ ID NO: 2, or a salt thereof; and
    (ii) (a) an agent for detecting insulin receptor or IRS protein, and an agent for detecting phosphorylated tyrosine or phosphorylated serine; (b) an agent for detecting tyrosine-phosphorylated IRS protein or insulin receptor; (c) an agent for detecting serine-phosphorylated IRS protein; or (d) KKA$^y$ mouse.

14. A kit for screening an agent for the treatment of diabetes by a method of screening an agent for the treatment of diabetes, wherein said method comprises:
    (i) preparing a cell line which expresses a protein comprising the amino acid sequence of SEQ ID NO: 1 or SEQ ID NO: 2, or a salt thereof;
    (ii) adding an antibody against the protein KKA$^y$ mouse adipose tissue homogenate or serum to the cell line so as to activate the protein;
    (iii) adding a test compound to the activated cell line and determining whether or not the test compound inactivates the protein; and
    (iv) selecting a test compound that inactivates the protein;
    wherein said inactivation of the protein is verified by monitoring phosphyorlation of the protein, phosphorylation of DAP12 intracellularly interacting with the protein, phosphorylation of ERK, or expression of TNF-α,
    wherein decreased phosphorylation or TNF-α expression is indicative of an agent for the treatment of diabetes, and
    wherein said kit comprises:
    (i) a cell capable of producing a protein comprising the amino acid sequence of SEQ ID NO: 1 or SEQ ID NO: 2, or a salt thereof; and
    (ii) (a) an agent for detecting insulin receptor or IRS protein, and an agent for detecting phosphorylated tyrosine or phosphorylated serine; (b) an agent for detecting tyrosine-phosphorylated IRS protein or insulin receptor; (c) an agent for detecting serine-phosphorylated IRS protein; or (d) KKA$^y$ mouse.

15. A method of screening an agent for the treatment of diabetes, which comprises:
    (i) preparing a cell line which expresses a protein comprising the amino acid sequence of SEQ ID NO: 2, or a salt thereof;
    (ii) adding an antibody against the protein, KKA$^y$ mouse adipose tissue homogenate or serum to the cell line so as to activate the protein;

(iii) adding a test compound to the activated cell line and determining whether or not the test compound inactivates the protein; and
(iv) selecting a test compound that inactivates the protein;
wherein said inactivation of the protein is verified by monitoring phosphyorlation of the protein, phosphorylation of DAP12 intracellularly interacting with the protein, phosphorylation of ERK, or expression of TNF-$\alpha$,
wherein decreased phosphorylation or TNF-$\alpha$ expression is indicative of an agent for the treatment of diabetes.

16. A kit for screening an agent for the treatment of diabetes by the method of claim 15, wherein said kit comprises a cell producing a protein comprising the amino acid sequence of SEQ ID NO: 2, or a salt thereof.

17. A kit for screening an insulin-sensitizing agent by the method of claim 2, wherein said kit comprises a cell producing a protein comprising the amino acid sequence of SEQ ID NO: 2, or a salt thereof.

* * * * *

SEQUENCE LISTING

```
<160> NUMBER OF SEQ ID NOS: 17

<210> SEQ ID NO 1
<211> LENGTH: 230
<212> TYPE: PRT
<213> ORGANISM: Homo sapiens

<400> SEQUENCE: 1

Met Glu Pro Leu Arg Leu Leu Ile Leu Leu Phe Val Thr Glu Leu Ser
 1               5                   10                  15
```

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Ile Pro Phe Pro Thr Ser Ile Leu
                165                 170                 175

Leu Leu Leu Ala Cys Ile Phe Leu Ile Lys Ile Leu Ala Ala Ser Ala
            180                 185                 190

Leu Trp Ala Ala Ala Trp His Gly Gln Lys Pro Gly Thr His Pro Pro
        195                 200                 205

Ser Glu Leu Asp Cys Gly His Asp Pro Gly Tyr Gln Leu Gln Thr Leu
    210                 215                 220

Pro Gly Leu Arg Asp Thr
225                 230

<210> SEQ ID NO 2
<211> LENGTH: 227
<212> TYPE: PRT
<213> ORGANISM: Mus musculus

<400> SEQUENCE: 2

Met Gly Pro Leu His Gln Phe Leu Leu Leu Ile Thr Ala Leu Ser
1               5                   10                  15

Gln Ala Leu Asn Thr Thr Val Leu Gln Gly Met Ala Gly Gln Ser Leu
            20                  25                  30

Arg Val Ser Cys Thr Tyr Asp Ala Leu Lys His Trp Gly Arg Arg Lys
        35                  40                  45

Ala Trp Cys Arg Gln Leu Gly Glu Glu Gly Pro Cys Gln Arg Val Val
    50                  55                  60

Ser Thr His Gly Val Trp Leu Leu Ala Phe Leu Lys Lys Arg Asn Gly
65                  70                  75                  80

Ser Thr Val Ile Ala Asp Asp Thr Leu Ala Gly Thr Val Thr Ile Thr
                85                  90                  95

Leu Lys Asn Leu Gln Ala Gly Asp Ser Gly Leu Tyr Gln Cys Gln Ser
            100                 105                 110

Leu Arg Gly Arg Glu Ala Glu Val Leu Lys Lys Val Leu Val Glu Val
        115                 120                 125

Leu Glu Asp Pro Leu Asp Asp Gln Asp Ala Gly Asp Leu Trp Val Pro
    130                 135                 140

Glu Glu Ser Glu Ser Phe Glu Gly Ala Gln Val Glu His Ser Thr Ser

```
                145                 150                 155                 160
Arg Asn Gln Glu Thr Ser Phe Pro Pro Thr Ser Ile Leu Leu Leu
                    165                 170                 175
Ala Cys Val Leu Leu Ser Lys Phe Leu Ala Ala Ser Ile Leu Trp Ala
                180                 185                 190
Val Ala Arg Gly Arg Gln Lys Pro Gly Thr Pro Val Val Arg Gly Leu
            195                 200                 205
Asp Cys Gly Gln Asp Ala Gly His Gln Leu Gln Ile Leu Thr Gly Pro
        210                 215                 220
Gly Gly Thr
225

<210> SEQ ID NO 3
<211> LENGTH: 690
<212> TYPE: DNA
<213> ORGANISM: Homo sapiens

<400> SEQUENCE: 3
atggagcctc tccggctgct catcttactc tttgtcacag agctgtccgg agcccacaac      60
accacagtgt tccagggcgt ggcgggccag tccctgcagg tgtcttgccc ctatgactcc     120
atgaagcact gggggaggcg caaggcctgg tgccgccagc tgggagagaa gggcccatgc     180
cagcgtgtgg tcagcacgca caacttgtgg ctgctgtcct tcctgaggag gtggaatggg     240
agcacagcca tcacagacga tacccctggt ggcactctca ccattacgct gcggaatcta     300
caaccccatg atgcgggtct ctaccagtgc cagagcctcc atggcagtga ggctgacacc     360
ctcaggaagg tcctggtgga ggtgctggca gaccccctgg atcaccggga tgctggagat     420
ctctggttcc ccggggagtc tgagagcttc gaggatgccc atgtggagca cagcatctcc     480
aggagcctct ggaaggagaa atccccttc ccacccactt ccatccttct cctcctggcc     540
tgcatctttc tcatcaagat tctagcagcc agcgccctct gggctgcagc ctggcatgga     600
cagaagccag ggacacatcc acccagtgaa ctggactgtg ccatgaccc agggtatcag     660 ctccaaactc tgccagggct gagagacacg                                      690

<210> SEQ ID NO 4
<211> LENGTH: 681
<212> TYPE: DNA
<213> ORGANISM: Mus musculus

<400> SEQUENCE: 4 atgggaccctc tccaccagtt tctcctgctg ctgatcacag ccctgtccca agccctcaac     60
accacggtgc tgcagggcat ggctggccag tccttgaggg tgtcatgtac ttatgacgcc     120
ttgaagcact gggggagacg caaggcctgg tgtcggcagc tgggtgagga gggcccatgc     180
cagcgtgtgg tgagcacaca cggtgtgtgg ctgctggcct tcctgaagaa gcggaatggg     240
agcacagtca tcgcagatga caccttgct ggaaccgtca ccatcactct gaagaacctc     300
caagccggtg actcgggcct ctaccagtgt cagagtctcc aggccgagag gctgaggtc     360 ctgaagaaag tactggtgga ggtgctggag gaccctctag atgaccaaga tgctggagat     420
ctctgggtcc ccgaggagtc agagagtttc gaggtgcccc aagtggaaca cagcacctcc     480
aggaatcaag agacctcctt cccacccacc tccattcttc tcctcctggc ctgcgttctc     540
ctgagcaagt tcttgcggc cagcatcctc tgggctgtgg ccaggggcag gcagaagcca     600
ggaacacctg tggtcagagg gctggactgt ggccaagatg ctgggcacca acttcagatc     660
```
ctcactggac ccggaggtac g     681

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgccagggtt ttcccagtca cgac     24

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agcggataac aatttcacac aggaaac     27

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atggagcctc tccggctgct catc     24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcacgtgtct ctcagccctg gcag     24

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atgggacctc tccaccagtt tctcctg     27

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcacgtacct ccgggtccag tgag     24

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acacccttgc tggaaccgtc ac                                           22

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtcctccagc acctccacca gta                                          23

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gagtctgaga gcttcgagga tg                                           22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctggctgcta gaatcttgat ga                                           22

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aagggatgag aagttcccaa a                                            21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctccacttgg tggtttgcta c                                            21

```
<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ser His Met
 1
```